(12) United States Patent
Siahaan et al.

(10) Patent No.: US 8,188,218 B2
(45) Date of Patent: May 29, 2012

(54) BI-FUNCTIONAL PEPTIDES FOR MULTIPLE SCLEROSIS TREATMENT AND DIAGNOSIS

(75) Inventors: Teruna J. Siahaan, Lawrence, KS (US); Naoki Kobayashi, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 11/588,645

(22) Filed: Oct. 27, 2006

(65) Prior Publication Data

US 2008/0103091 A1    May 1, 2008

(51) Int. Cl.
*A61K 38/16*    (2006.01)
*C07K 14/435*    (2006.01)
*C12P 21/00*    (2006.01)

(52) U.S. Cl. ...................................... 530/324; 435/69.7
(58) Field of Classification Search .......................... None
See application file for complete search history.

(56) References Cited

U.S. PATENT DOCUMENTS

2005/0107585 A1    5/2005    Murray et al.

OTHER PUBLICATIONS

Stoeckle et al., Results Probl Cell Differ, 51:149-72, 2010.*
McRae et al., J Neuroimmunol., 60:17-28, 1995.*
Kobayashi et al., "Antigen-Specific Suppression of Experimental Autoimmune Encephalomyeliltis by a Novel Bifunctional Peptide Inhibitor". The Journal of Pharmacology and Experimental Therapeutics. May 23, 2007, vol. 322, pp. 879-886.
Anderson et al., "Targeting ICAM-1/LFA-1 Interaction for Controlling Autoimmune Diseases: Designing Peptide and Same Molecule Inhibitors." Peptides. Mar. 2003, vol. 23, Issue 3, pp. 487-501.

* cited by examiner

*Primary Examiner* — Daniel E Kolker
*Assistant Examiner* — Stacey MacFarlane
(74) *Attorney, Agent, or Firm* — Stinson Morrison Hecker LLP

(57) ABSTRACT

Novel bifunctional peptides useful in the treatment and/or diagnosis of EAE or MS. The peptides have a first peptide portion derived from an epitope of myelin proteolipid protein, myelin oligodendrocyte glycoprotein, or oligodendrocyte-specific peptide and a second peptide portion derived from CD11a (LFA-1 alpha subunit), CD18 (LFA-1 beta subunit), CD154 (CD40L), Fas-Ligand, or CTLA4. The carboxy and/or amino termini of the bifunctional peptides may be modified.

17 Claims, 13 Drawing Sheets

Disease development

Incidence of EAE

※ Onset of EAE was defined by a score of >0.5 or 0.5 for two sequential days.

Changes in body weight

Binding Scheme of Biotin-PLP-BPI

Incubation of peptide(s) with LS102.9 cells or spleen B cells
↓ 37°C 5%CO₂, 14–16 hr
Wash×3
Incubation with <u>fluorescein-avidin (15 ug/ml)</u>
↓ 4°C, 30 min
Wash×3
Incubation with <u>biotinylated anti-avidin (3 ug/ml)</u>
↓ 4°C, 30-60 min
Wash×3
Incubation with <u>fluorescein-avidin (15 ug/ml)</u>
↓ 4°C, 30 min
Wash×3
Flow cytometry Nanoparticles with PLP-BPI attached loaded with Gd$^{3+}$ or iron oxide. Particle can be formed from PLGA. PLP-BPI can be attached to PLGA via a linker as shown below.

Particle-PLP-BPI Conjugation Chemistry

```
                        SEQUENCE LISTING

<160> NUMBER OF SEQ ID NOS: 91

<210> SEQ ID NO 1
<211> LENGTH: 13
<212> TYPE: PRT
<213> ORGANISM: Homo sapiens

<400> SEQUENCE: 1

His Cys Leu Gly Lys Trp Leu Gly His Pro Asp Lys Phe
1               5                   10

<210> SEQ ID NO 2
<211> LENGTH: 13
<212> TYPE: PRT
<213> ORGANISM: Homo sapiens

<400> SEQUENCE: 2

His Ser Leu Gly Lys Trp Leu Gly His Pro Asp Lys Phe
1               5                   10

<210> SEQ ID NO 3
<211> LENGTH: 13
<212> TYPE: PRT
<213> ORGANISM: Homo sapiens

<400> SEQUENCE: 3

His Ser Leu Gly Lys Gln Leu Gly His Pro Asp Lys Phe
1               5                   10

<210> SEQ ID NO 4
<211> LENGTH: 13
<212> TYPE: PRT
<213> ORGANISM: Homo sapiens
```

```
<400> SEQUENCE: 4

His Ser Leu Gly Lys Leu Leu Gly Arg Pro Asp Lys Phe
1               5                   10

<210> SEQ ID NO 5
<211> LENGTH: 13
<212> TYPE: PRT
<213> ORGANISM: Homo sapiens

<400> SEQUENCE: 5

His Ser Leu Gly Lys Trp Asp Gly His Pro Asp Lys Phe
1               5                   10

<210> SEQ ID NO 6
<211> LENGTH: 21
<212> TYPE: PRT
<213> ORGANISM: Homo sapiens

<400> SEQUENCE: 6

Leu Thr Gly Thr Glu Lys Leu Ile Glu Thr Tyr Phe Ser Lys Asn Tyr
1               5                   10                  15

Gln Asp Tyr Glu Tyr
            20

<210> SEQ ID NO 7
<211> LENGTH: 18
<212> TYPE: PRT
<213> ORGANISM: Homo sapiens

<400> SEQUENCE: 7

Glu Gly Phe Tyr Thr Thr Gly Ala Val Arg Gln Ile Phe Gly Asp Tyr
1               5                   10                  15

Lys Thr

<210> SEQ ID NO 8
<211> LENGTH: 32
<212> TYPE: PRT
<213> ORGANISM: Homo sapiens

<400> SEQUENCE: 8

Cys Phe Phe Gly Val Ala Leu Phe Cys Gly Cys Gly His Glu Ala Leu
1               5                   10                  15

Thr Gly Thr Glu Lys Leu Ile Glu Thr Tyr Phe Ser Lys Asn Tyr Gln
                20                  25                  30

<210> SEQ ID NO 9
<211> LENGTH: 32
<212> TYPE: PRT
<213> ORGANISM: Homo sapiens

<400> SEQUENCE: 9

Gly Lys Val Cys Gly Ser Asn Leu Leu Ser Ile Cys Lys Thr Ala Glu
1               5                   10                  15

Phe Gln Met Thr Phe His Leu Phe Ile Ala Ala Phe Val Gly Ala Ala
                20                  25                  30

<210> SEQ ID NO 10
<211> LENGTH: 20
<212> TYPE: PRT
<213> ORGANISM: Homo sapiens
```

```
<400> SEQUENCE: 10

Phe Met Ile Ala Ala Thr Tyr Asn Phe Ala Val Leu Lys Leu Met Gly
1               5                   10                  15

Arg Gly Thr Lys
            20

<210> SEQ ID NO 11
<211> LENGTH: 20
<212> TYPE: PRT
<213> ORGANISM: Homo sapiens

<400> SEQUENCE: 11

Phe Tyr Thr Thr Gly Ala Val Arg Gln Ile Phe Gly Asp Tyr Lys Thr
1               5                   10                  15

Thr Ile Cys Gly
            20

<210> SEQ ID NO 12
<211> LENGTH: 22
<212> TYPE: PRT
<213> ORGANISM: Homo sapiens

<400> SEQUENCE: 12

Thr Glu Lys Leu Ile Glu Thr Tyr Phe Ser Lys Asn Tyr Gln Asp Tyr
1               5                   10                  15

Glu Tyr Leu Ile Asn Val
            20

<210> SEQ ID NO 13
<211> LENGTH: 14
<212> TYPE: PRT
<213> ORGANISM: Homo sapiens

<400> SEQUENCE: 13

Lys Thr Thr Ile Cys Gly Lys Gly Leu Ser Ala Thr Val Thr
1               5                   10

<210> SEQ ID NO 14
<211> LENGTH: 15
<212> TYPE: PRT
<213> ORGANISM: Homo sapiens

<400> SEQUENCE: 14

Asp Tyr Glu Tyr Leu Ile Asn Val Ile His Ala Phe Gln Tyr Val
1               5                   10                  15

<210> SEQ ID NO 15
<211> LENGTH: 14
<212> TYPE: PRT
<213> ORGANISM: Homo sapiens

<400> SEQUENCE: 15

Asn Thr Trp Thr Thr Cys Gln Ser Ile Ala Phe Pro Ser Lys
1               5                   10

<210> SEQ ID NO 16
<211> LENGTH: 14
<212> TYPE: PRT
<213> ORGANISM: Homo sapiens
```

```
<400> SEQUENCE: 16

Pro Gly Tyr Pro Ile Arg Ala Leu Val Gly Asp Glu Ala Glu
1               5                   10

<210> SEQ ID NO 17
<211> LENGTH: 21
<212> TYPE: PRT
<213> ORGANISM: Mus musculus x Rattus norvegicus

<400> SEQUENCE: 17

Met Glu Val Gly Trp Tyr Arg Ser Pro Phe Ser Arg Val Val His Leu
1               5                   10                  15

Tyr Arg Asn Gly Lys
            20

<210> SEQ ID NO 18
<211> LENGTH: 12
<212> TYPE: PRT
<213> ORGANISM: Homo sapiens

<400> SEQUENCE: 18

Thr Cys Phe Phe Arg Asp His Ser Tyr Gln Glu Glu
1               5                   10

<210> SEQ ID NO 19
<211> LENGTH: 20
<212> TYPE: PRT
<213> ORGANISM: Homo sapiens

<400> SEQUENCE: 19

Val Thr Ser Phe Val Gly Trp Ile Gly Val Ile Val Thr Thr Ser Thr
1               5                   10                  15

Asn Asp Trp Val
            20

<210> SEQ ID NO 20
<211> LENGTH: 20
<212> TYPE: PRT
<213> ORGANISM: Homo sapiens

<400> SEQUENCE: 20

Ile Val Thr Thr Ser Thr Asn Asp Trp Val Val Thr Cys Gly Tyr Thr
1               5                   10                  15

Ile Pro Thr Cys
            20

<210> SEQ ID NO 21
<211> LENGTH: 20
<212> TYPE: PRT
<213> ORGANISM: Homo sapiens

<400> SEQUENCE: 21

Val Thr Cys Gly Tyr Thr Ile Pro Thr Cys Arg Lys Leu Asp Glu Leu
1               5                   10                  15

Gly Ser Lys Gly
            20

<210> SEQ ID NO 22
<211> LENGTH: 20
<212> TYPE: PRT
<213> ORGANISM: Homo sapiens
```

```
<400> SEQUENCE: 22

Arg Lys Leu Asp Glu Leu Gly Ser Lys Gly Leu Trp Ala Asp Cys Val
1               5                   10                  15

Met Ala Thr Gly
            20

<210> SEQ ID NO 23
<211> LENGTH: 20
<212> TYPE: PRT
<213> ORGANISM: Homo sapiens

<400> SEQUENCE: 23

Leu Trp Ala Asp Cys Val Met Ala Thr Gly Leu Tyr His Cys Lys Pro
1               5                   10                  15

Leu Val Asp Ile
            20

<210> SEQ ID NO 24
<211> LENGTH: 20
<212> TYPE: PRT
<213> ORGANISM: Homo sapiens

<400> SEQUENCE: 24

Leu Tyr His Cys Lys Pro Leu Val Asp Ile Leu Ile Leu Pro Gly Tyr
1               5                   10                  15

Val Gln Ala Cys
            20

<210> SEQ ID NO 25
<211> LENGTH: 20
<212> TYPE: PRT
<213> ORGANISM: Homo sapiens

<400> SEQUENCE: 25

Leu Ile Leu Pro Gly Tyr Val Gln Ala Cys Arg Ala Leu Met Ile Ala
1               5                   10                  15

Ala Ser Val Leu
            20

<210> SEQ ID NO 26
<211> LENGTH: 20
<212> TYPE: PRT
<213> ORGANISM: Homo sapiens

<400> SEQUENCE: 26

Arg Ala Leu Met Ile Ala Ala Ser Val Leu Gly Leu Pro Ala Ile Leu
1               5                   10                  15

Leu Leu Leu Thr
            20

<210> SEQ ID NO 27
<211> LENGTH: 20
<212> TYPE: PRT
<213> ORGANISM: Homo sapiens

<400> SEQUENCE: 27

Gly Leu Pro Ala Ile Leu Leu Leu Leu Thr Val Leu Pro Cys Ile Arg
1               5                   10                  15

Met Gly Gln Glu
            20
```

```
<210> SEQ ID NO 28
<211> LENGTH: 20
<212> TYPE: PRT
<213> ORGANISM: Homo sapiens

<400> SEQUENCE: 28

Val Leu Pro Cys Ile Arg Met Gly Gln Glu Pro Gly Val Ala Lys Tyr
1               5                   10                  15
Arg Arg Ala Gln
            20

<210> SEQ ID NO 29
<211> LENGTH: 20
<212> TYPE: PRT
<213> ORGANISM: Homo sapiens

<400> SEQUENCE: 29

Pro Gly Val Ala Lys Tyr Arg Arg Ala Gln Leu Ala Gly Val Leu Leu
1               5                   10                  15
Ile Leu Leu Ala
            20

<210> SEQ ID NO 30
<211> LENGTH: 20
<212> TYPE: PRT
<213> ORGANISM: Homo sapiens

<400> SEQUENCE: 30

Leu Cys Ala Leu Val Ala Thr Ile Trp Phe Pro Val Cys Ala His Arg
1               5                   10                  15
Glu Thr Thr Ile
            20

<210> SEQ ID NO 31
<211> LENGTH: 20
<212> TYPE: PRT
<213> ORGANISM: Homo sapiens

<400> SEQUENCE: 31

Val Ser Phe Gly Tyr Ser Leu Tyr Ala Gly Trp Ile Gly Ala Val Leu
1               5                   10                  15
Cys Leu Val Gly
            20

<210> SEQ ID NO 32
<211> LENGTH: 20
<212> TYPE: PRT
<213> ORGANISM: Homo sapiens

<400> SEQUENCE: 32

Trp Ile Gly Ala Val Leu Cys Leu Val Gly Gly Cys Val Ile Leu Cys
1               5                   10                  15
Cys Ala Gly Asp
            20

<210> SEQ ID NO 33
<211> LENGTH: 20
<212> TYPE: PRT
<213> ORGANISM: Homo sapiens
```

-continued

```
<400> SEQUENCE: 33

Gly Cys Val Ile Leu Cys Cys Ala Gly Asp Ala Gln Ala Phe Gly Glu
1               5                   10                  15

Asn Val Ser Thr
            20

<210> SEQ ID NO 34
<211> LENGTH: 20
<212> TYPE: PRT
<213> ORGANISM: Homo sapiens

<400> SEQUENCE: 34

Ala Gln Ala Phe Gly Glu Asn Val Ser Thr Thr Leu Arg Ala Leu Ala
1               5                   10                  15

Pro Arg Leu Met
            20

<210> SEQ ID NO 35
<211> LENGTH: 20
<212> TYPE: PRT
<213> ORGANISM: Homo sapiens

<400> SEQUENCE: 35

Thr Leu Arg Ala Leu Ala Pro Arg Leu Met Arg Arg Val Pro Thr Tyr
1               5                   10                  15

Lys Arg Ala Ala
            20

<210> SEQ ID NO 36
<211> LENGTH: 17
<212> TYPE: PRT
<213> ORGANISM: Homo sapiens

<400> SEQUENCE: 36

Arg Arg Val Pro Thr Tyr Lys Arg Ala Ala Arg Leu Pro Thr Glu Val
1               5                   10                  15

Glu

<210> SEQ ID NO 37
<211> LENGTH: 20
<212> TYPE: PRT
<213> ORGANISM: Mus musculus

<400> SEQUENCE: 37

Val Thr Ser Phe Val Gly Trp Ile Gly Ile Ile Val Thr Thr Ser Thr
1               5                   10                  15

Asn Asp Trp Val
            20

<210> SEQ ID NO 38
<211> LENGTH: 20
<212> TYPE: PRT
<213> ORGANISM: Mus musculus

<400> SEQUENCE: 38

Ile Val Thr Thr Ser Thr Asn Asp Trp Val Val Thr Cys Ser Tyr Thr
1               5                   10                  15

Ile Pro Thr Cys
            20
```

```
<210> SEQ ID NO 39
<211> LENGTH: 20
<212> TYPE: PRT
<213> ORGANISM: Mus musculus

<400> SEQUENCE: 39

Val Thr Cys Ser Tyr Thr Ile Pro Thr Cys Arg Lys Met Asp Glu Leu
1               5                   10                  15

Gly Ser Lys Gly
            20

<210> SEQ ID NO 40
<211> LENGTH: 20
<212> TYPE: PRT
<213> ORGANISM: Mus musculus

<400> SEQUENCE: 40

Arg Lys Met Asp Glu Leu Gly Ser Lys Gly Leu Trp Ala Asp Cys Val
1               5                   10                  15

Met Ala Thr Gly
            20

<210> SEQ ID NO 41
<211> LENGTH: 20
<212> TYPE: PRT
<213> ORGANISM: Mus musculus

<400> SEQUENCE: 41

Gly Leu Pro Ala Ile Leu Leu Leu Leu Thr Val Leu Pro Cys Ile Arg
1               5                   10                  15

Met Gly His Glu
            20

<210> SEQ ID NO 42
<211> LENGTH: 20
<212> TYPE: PRT
<213> ORGANISM: Mus musculus

<400> SEQUENCE: 42

Val Leu Pro Cys Ile Arg Met Gly His Glu Pro Gly Val Ala Lys Tyr
1               5                   10                  15

Arg Arg Ala Gln
            20

<210> SEQ ID NO 43
<211> LENGTH: 20
<212> TYPE: PRT
<213> ORGANISM: Mus musculus

<400> SEQUENCE: 43

Leu Cys Ala Ile Val Ala Thr Ile Trp Phe Pro Val Cys Ala His Arg
1               5                   10                  15

Glu Ile Thr Ile
            20

<210> SEQ ID NO 44
<211> LENGTH: 20
<212> TYPE: PRT
<213> ORGANISM: Mus musculus
```

-continued

```
<400> SEQUENCE: 44

Pro Val Cys Ala His Arg Glu Ile Thr Ile Val Ser Phe Gly Tyr Ser
1               5                   10                  15

Leu Tyr Ala Gly
            20

<210> SEQ ID NO 45
<211> LENGTH: 20
<212> TYPE: PRT
<213> ORGANISM: Mus musculus

<400> SEQUENCE: 45

Gly Cys Val Ile Val Cys Cys Ser Gly Asp Ala Gln Ser Phe Gly Glu
1               5                   10                  15

Asn Arg Phe Tyr
            20

<210> SEQ ID NO 46
<211> LENGTH: 20
<212> TYPE: PRT
<213> ORGANISM: Mus musculus

<400> SEQUENCE: 46

Ala Gln Ser Phe Gly Glu Asn Arg Phe Tyr Tyr Ser Ser Gly Ser Ser
1               5                   10                  15

Ser Pro Thr His
            20

<210> SEQ ID NO 47
<211> LENGTH: 17
<212> TYPE: PRT
<213> ORGANISM: Mus musculus

<400> SEQUENCE: 47

Tyr Tyr Ser Ser Gly Ser Ser Pro Thr His Ala Lys Ser Ala His
1               5                   10                  15

Val

<210> SEQ ID NO 48
<211> LENGTH: 24
<212> TYPE: PRT
<213> ORGANISM: Homo sapiens

<400> SEQUENCE: 48

Ile Thr Asp Gly Glu Ala Thr Asp Ser Gly Asn Ile Asp Ala Ala Lys
1               5                   10                  15

Asp Ile Ile Tyr Ile Ile Gly Ile
            20

<210> SEQ ID NO 49
<211> LENGTH: 10
<212> TYPE: PRT
<213> ORGANISM: Homo sapiens

<400> SEQUENCE: 49

Ile Thr Asp Gly Glu Ala Thr Asp Ser Gly
1               5                   10

<210> SEQ ID NO 50
<211> LENGTH: 10
<212> TYPE: PRT
<213> ORGANISM: Homo sapiens
```

```
<400> SEQUENCE: 50

Thr Asp Gly Glu Ala Thr Asp Ser Gly Asn
1               5                   10

<210> SEQ ID NO 51
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.  Pen and Cys residues were
      added to the N- and C-terminus for forming a disulfide bond
      between Pen1 to Cys 12.
<220> FEATURE:
<221> NAME/KEY: MOD_RES
<222> LOCATION: (1)..(1)
<223> OTHER INFORMATION: X=penicillamine

<400> SEQUENCE: 51

Xaa Ile Thr Asp Gly Glu Ala Thr Asp Ser Gly Cys
1               5                   10

<210> SEQ ID NO 52
<211> LENGTH: 6
<212> TYPE: PRT
<213> ORGANISM: Homo sapiens

<400> SEQUENCE: 52

Ile Thr Asp Gly Glu Ala
1               5

<210> SEQ ID NO 53
<211> LENGTH: 6
<212> TYPE: PRT
<213> ORGANISM: Homo sapiens

<400> SEQUENCE: 53

Thr Asp Gly Glu Ala Thr
1               5

<210> SEQ ID NO 54
<211> LENGTH: 6
<212> TYPE: PRT
<213> ORGANISM: Homo sapiens

<400> SEQUENCE: 54

Asp Gly Glu Ala Thr Asp
1               5

<210> SEQ ID NO 55
<211> LENGTH: 6
<212> TYPE: PRT
<213> ORGANISM: Homo sapiens

<400> SEQUENCE: 55

Gly Glu Ala Thr Asp Ser
1               5

<210> SEQ ID NO 56
<211> LENGTH: 6
<212> TYPE: PRT
<213> ORGANISM: Homo sapiens

<400> SEQUENCE: 56

Glu Ala Thr Asp Ser Gly
1               5
```

```
<210> SEQ ID NO 57
<211> LENGTH: 6
<212> TYPE: PRT
<213> ORGANISM: Homo sapiens
<220> FEATURE:
<221> NAME/KEY: MISC_FEATURE
<223> OTHER INFORMATION: Cyclic Peptide.  N- to C-terminal cyclization.

<400> SEQUENCE: 57

Ile Thr Asp Gly Glu Ala
1               5

<210> SEQ ID NO 58
<211> LENGTH: 6
<212> TYPE: PRT
<213> ORGANISM: Homo sapiens
<220> FEATURE:
<221> NAME/KEY: MISC_FEATURE
<223> OTHER INFORMATION: Cyclic Peptide.  N- to C-terminal cyclization
      with K mutation at residue 6

<400> SEQUENCE: 58

Ile Thr Asp Gly Glu Lys
1               5

<210> SEQ ID NO 59
<211> LENGTH: 10
<212> TYPE: PRT
<213> ORGANISM: Homo sapiens

<400> SEQUENCE: 59

Asp Ser Gly Asn Ile Asp Ala Ala Lys Asp
1               5                   10

<210> SEQ ID NO 60
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.  Pen and Cys residues were
      added to the N- and C-terminus for forming a disulfide bond
      between Pen1 to Cys12.
<220> FEATURE:
<221> NAME/KEY: MOD_RES
<222> LOCATION: (1)..(1)
<223> OTHER INFORMATION: X=penicillamine

<400> SEQUENCE: 60

Xaa Asp Ser Gly Asn Ile Asp Ala Ala Lys Asp Cys
1               5                   10

<210> SEQ ID NO 61
<211> LENGTH: 10
<212> TYPE: PRT
<213> ORGANISM: Homo sapiens

<400> SEQUENCE: 61

Ala Lys Asp Ile Ile Tyr Ile Ile Gly Ile
1               5                   10

<210> SEQ ID NO 62
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.  Pen and Cys residues were
      added to the N- and C-terminus for forming a disulfide bond
      between Pen1 to Cys12.
```

```
<220> FEATURE:
<221> NAME/KEY: MOD_RES
<222> LOCATION: (1)..(1)
<223> OTHER INFORMATION: X=penicillamine

<400> SEQUENCE: 62

Xaa Ala Lys Asp Ile Ile Tyr Ile Ile Gly Ile Cys
1               5                   10

<210> SEQ ID NO 63
<211> LENGTH: 24
<212> TYPE: PRT
<213> ORGANISM: Homo sapiens

<400> SEQUENCE: 63

Gly Val Asp Val Asp Gln Asp Gly Glu Thr Glu Leu Ile Gly Ala Pro
1               5                   10                  15

Leu Tyr Phe Gly Glu Gln Arg Gly
            20

<210> SEQ ID NO 64
<211> LENGTH: 10
<212> TYPE: PRT
<213> ORGANISM: Homo sapiens

<400> SEQUENCE: 64

Gly Val Asp Val Asp Gln Asp Gly Glu Thr
1               5                   10

<210> SEQ ID NO 65
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.
<220> FEATURE:
<221> NAME/KEY: MOD_RES
<222> LOCATION: (1)..(1)
<223> OTHER INFORMATION: X=penicillamine

<400> SEQUENCE: 65

Xaa Gly Val Asp Val Asp Gln Asp Gly Glu Thr Cys
1               5                   10

<210> SEQ ID NO 66
<211> LENGTH: 11
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X=penicillamine

<400> SEQUENCE: 66

Xaa Gly Glu Thr Glu Leu Ile Gly Ala Pro Leu
1               5                   10

<210> SEQ ID NO 67
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.
<220> FEATURE:
<221> NAME/KEY: MOD_RES
<222> LOCATION: (1)..(1)
<223> OTHER INFORMATION: X=penicillamine
```

```
<400> SEQUENCE: 67

Xaa Gly Glu Thr Glu Leu Ile Gly Ala Pro Leu Cys
 1               5                  10

<210> SEQ ID NO 68
<211> LENGTH: 10
<212> TYPE: PRT
<213> ORGANISM: Homo sapiens

<400> SEQUENCE: 68

Ala Pro Leu Phe Tyr Gly Glu Gln Arg Gly
 1               5                  10

<210> SEQ ID NO 69
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.
<220> FEATURE:
<221> NAME/KEY: MOD_RES
<222> LOCATION: (1)..(1)
<223> OTHER INFORMATION: X=penicillamine

<400> SEQUENCE: 69

Xaa Ala Pro Leu Phe Tyr Gly Glu Gln Arg Gly Cys
 1               5                  10

<210> SEQ ID NO 70
<211> LENGTH: 25
<212> TYPE: PRT
<213> ORGANISM: Homo sapiens

<400> SEQUENCE: 70

Asp Leu Ser Tyr Ser Leu Asp Asp Leu Arg Asn Val Lys Lys Leu Gly
 1               5                  10                  15

Gly Asp Leu Leu Arg Ala Leu Asn Glu
                20                  25

<210> SEQ ID NO 71
<211> LENGTH: 10
<212> TYPE: PRT
<213> ORGANISM: Homo sapiens

<400> SEQUENCE: 71

Asp Leu Ser Tyr Ser Leu Asp Asp Leu Arg
 1               5                  10

<210> SEQ ID NO 72
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.
<220> FEATURE:
<221> NAME/KEY: MOD_RES
<222> LOCATION: (1)..(1)
<223> OTHER INFORMATION: X=penicillamine

<400> SEQUENCE: 72

Xaa Asp Leu Ser Tyr Ser Leu Asp Asp Leu Arg Cys
 1               5                  10
```

```
<210> SEQ ID NO 73
<211> LENGTH: 10
<212> TYPE: PRT
<213> ORGANISM: Homo sapiens

<400> SEQUENCE: 73

Asp Leu Arg Asn Val Lys Lys Leu Gly Gly
1               5                   10

<210> SEQ ID NO 74
<211> LENGTH: 12
<212> TYPE: PRT
<213> ORGANISM: Homo sapiens
<220> FEATURE:
<221> NAME/KEY: MISC_FEATURE
<223> OTHER INFORMATION: Cyclic Peptide.
<220> FEATURE:
<221> NAME/KEY: MOD_RES
<222> LOCATION: (1)..(1)
<223> OTHER INFORMATION: X=penicillamine

<400> SEQUENCE: 74

Xaa Asp Leu Arg Asn Val Lys Lys Leu Gly Gly Cys
1               5                   10

<210> SEQ ID NO 75
<211> LENGTH: 10
<212> TYPE: PRT
<213> ORGANISM: Homo sapiens

<400> SEQUENCE: 75

Gly Gly Asp Leu Leu Arg Ala Leu Asn Glu
1               5                   10

<210> SEQ ID NO 76
<211> LENGTH: 12
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X=penicillamine

<400> SEQUENCE: 76

Xaa Gly Gly Asp Leu Leu Arg Ala Leu Asn Glu Cys
1               5                   10

<210> SEQ ID NO 77
<211> LENGTH: 10
<212> TYPE: PRT
<213> ORGANISM: Homo sapiens

<400> SEQUENCE: 77

Ala Ser Pro Gly Lys Ala Thr Glu Val Arg
1               5                   10

<210> SEQ ID NO 78
<211> LENGTH: 10
<212> TYPE: PRT
<213> ORGANISM: Mus musculus

<400> SEQUENCE: 78

Ser Pro Ser His Asn Thr Asp Glu Val Arg
1               5                   10
```

<210> SEQ ID NO 79
<211> LENGTH: 12
<212> TYPE: PRT
<213> ORGANISM: Homo sapiens

<400> SEQUENCE: 79

Lys Val Glu Leu Met Tyr Pro Pro Pro Tyr Tyr Leu
1               5                   10

<210> SEQ ID NO 80
<211> LENGTH: 12
<212> TYPE: PRT
<213> ORGANISM: Mus musculus

<400> SEQUENCE: 80

Lys Val Glu Leu Met Tyr Pro Pro Pro Tyr Phe Val
1               5                   10

<210> SEQ ID NO 81
<211> LENGTH: 10
<212> TYPE: PRT
<213> ORGANISM: Mus musculus

<400> SEQUENCE: 81

Ile Thr Asp Gly Glu Ala Thr Asp Ser Gly
1               5                   10

<210> SEQ ID NO 82
<211> LENGTH: 13
<212> TYPE: PRT
<213> ORGANISM: Homo sapiens

<400> SEQUENCE: 82

Lys Gly Tyr Tyr Thr Met Ser Asn Asn Leu Val Thr Leu
1               5                   10

<210> SEQ ID NO 83
<211> LENGTH: 13
<212> TYPE: PRT
<213> ORGANISM: Mus musculus

<400> SEQUENCE: 83

Lys Gly Tyr Tyr Thr Met Ser Asn Asn Leu Val Thr Leu
1               5                   10

<210> SEQ ID NO 84
<211> LENGTH: 16
<212> TYPE: PRT
<213> ORGANISM: Homo sapiens

<400> SEQUENCE: 84

Tyr Met Arg Asn Ser Lys Tyr Arg Ala Gly Gly Ala Tyr Gly Pro Gly
1               5                   10                  15

<210> SEQ ID NO 85
<211> LENGTH: 16
<212> TYPE: PRT
<213> ORGANISM: Mus musculus

<400> SEQUENCE: 85

Tyr Met Arg Asn Ser Lys Tyr Arg Ala Gly Gly Ala Tyr Gly Pro Gly
1               5                   10                  15

```
<210> SEQ ID NO 86
<211> LENGTH: 28
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: X=AMINOCAPROIC ACID
<220> FEATURE:
<221> NAME/KEY: MOD_RES
<222> LOCATION: (16)..(16)
<223> OTHER INFORMATION: X=AMINOCAPROIC ACID
<220> FEATURE:
<221> NAME/KEY: MOD_RES
<222> LOCATION: (18)..(18)
<223> OTHER INFORMATION: X=AMINOCAPROIC ACID

<400> SEQUENCE: 86

His Ser Leu Gly Lys Trp Leu Gly His Pro Asp Lys Phe Xaa Gly Xaa
 1               5                  10                  15

Gly Xaa Ile Thr Asp Gly Glu Ala Thr Asp Ser Gly
            20                  25

<210> SEQ ID NO 87
<211> LENGTH: 27
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: X=AMINOCAPROIC ACID
<220> FEATURE:
<221> NAME/KEY: MOD_RES
<222> LOCATION: (15)..(15)
<223> OTHER INFORMATION: X=AMINOCAPROIC ACID
<220> FEATURE:
<221> NAME/KEY: MOD_RES
<222> LOCATION: (17)..(17)
<223> OTHER INFORMATION: X=AMINOCAPROIC ACID

<400> SEQUENCE: 87

Ala Val His Ala Ala His Ala Glu Ile Asn Glu Ala Xaa Gly Xaa Gly
 1               5                  10                  15

Xaa Ile Thr Asp Gly Glu Ala Thr Asp Ser Gly
            20                  25

<210> SEQ ID NO 88
<211> LENGTH: 29
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X=AMINOCAPROIC ACID
<220> FEATURE:
<221> NAME/KEY: MOD_RES
<222> LOCATION: (15)..(15)
<223> OTHER INFORMATION: X=AMINOCAPROIC ACID
<220> FEATURE:
<221> NAME/KEY: MOD_RES
<222> LOCATION: (17)..(17)
<223> OTHER INFORMATION: X=AMINOCAPROIC ACID
<220> FEATURE:
<221> NAME/KEY: MOD_RES
<222> LOCATION: (19)..(19)
<223> OTHER INFORMATION: X=AMINOCAPROIC ACID

<400> SEQUENCE: 88

Xaa His Ser Leu Gly Lys Trp Leu Gly His Pro Asp Lys Phe Xaa Gly
 1               5                  10                  15

Xaa Gly Xaa Ile Thr Asp Gly Glu Ala Thr Asp Ser Gly
            20                  25
```

```
<210> SEQ ID NO 89
<211> LENGTH: 28
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: X=AMINOCAPROIC ACID
<220> FEATURE:
<221> NAME/KEY: MOD_RES
<222> LOCATION: (16)..(16)
<223> OTHER INFORMATION: X=AMINOCAPROIC ACID
<220> FEATURE:
<221> NAME/KEY: MOD_RES
<222> LOCATION: (18)..(18)
<223> OTHER INFORMATION: X=AMINOCAPROIC ACID

<400> SEQUENCE: 89

Gln Glu Ala Phe Ser His Ile Arg Ile Pro Leu Pro His Xaa Gly Xaa
1               5                   10                  15

Gly Xaa Ile Thr Asp Gly Glu Ala Thr Asp Ser Gly
            20                  25

<210> SEQ ID NO 90
<211> LENGTH: 29
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: X=N-gamma-(N-biotinyl-3-(2-(2-(3-
      aminopropyloxy)-ethoxy)-ethoxy)-propyl)-L-glutamine.
<220> FEATURE:
<221> NAME/KEY: MOD_RES
<222> LOCATION: (15)..(15)
<223> OTHER INFORMATION: X=AMINOCAPROIC ACID
<220> FEATURE:
<221> NAME/KEY: MOD_RES
<222> LOCATION: (17)..(17)
<223> OTHER INFORMATION: X=AMINOCAPROIC ACID
<220> FEATURE:
<221> NAME/KEY: MOD_RES
<222> LOCATION: (19)..(19)
<223> OTHER INFORMATION: X=AMINOCAPROIC ACID

<400> SEQUENCE: 90

Xaa His Ser Leu Gly Lys Trp Leu Gly His Pro Asp Lys Phe Xaa Gly
1               5                   10                  15

Xaa Gly Xaa Ile Thr Asp Gly Glu Ala Thr Asp Ser Gly
            20                  25

<210> SEQ ID NO 91
<211> LENGTH: 28
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: X=AMINOCAPROIC ACID
<220> FEATURE:
<221> NAME/KEY: MOD_RES
<222> LOCATION: (15)..(15)
<223> OTHER INFORMATION: X=N-gamma-(N-biotinyl-3-(2-(2-(3-
      aminopropyloxy)-ethoxy)-ethoxy)-propyl)-L-glutamine.
<220> FEATURE:
<221> NAME/KEY: MOD_RES
<222> LOCATION: (16)..(16)
<223> OTHER INFORMATION: X=AMINOCAPROIC ACID
<220> FEATURE:
<221> NAME/KEY: MOD_RES
<222> LOCATION: (18)..(18)
<223> OTHER INFORMATION: X=AMINOCAPROIC ACID
```

```
<400> SEQUENCE: 91

His Ser Leu Gly Lys Trp Leu Gly His Pro Asp Lys Phe Xaa Xaa Xaa
1               5                   10                  15

Gly Xaa Ile Thr Asp Gly Glu Ala Thr Asp Ser Gly
            20                  25
```

BI-FUNCTIONAL PEPTIDES FOR MULTIPLE SCLEROSIS TREATMENT AND DIAGNOSIS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

In general, a two-signal mechanism is required to fully activate the T-cell. Signal-1 occurs when the T-cell antigen receptor ("TCR") recognizes the peptide:MHC-II complex on the surface of an antigen presenting cell ("APC"). This first signal passes through the T-cell receptor and initiates a cascade of tyrosine phosphorylation/dephosphorylation events mediated by kinases and phosphatases and leads to the activation of calcium flux, nuclear factor of activated T-cells ("NF-AT") and NF-κB transcription factors. These factors enter the nucleus of the T-cell and bind to promoters of genes responsible for effector functions. Signal-2 arises from the binding of Signal-2 receptors on the surface of T-cells to their ligands on the surface of an APC. Signal-2 receptors include CD28 and its ligand B7 as well as LFA-1 (CD11a/CD18) and its ligand ICAM-1. When a Signal-2 receptor and its ligand form a complex at the interface between the T-cell and APC receptor membranes, a series of signaling events occur. These events include serine/threonine phosphorylation/dephosphorylation and activation of guanine nucleotide exchange factors that activate adapter proteins with GTPase activity.

A defining stage of the immune response is the differentiation of CD4+ T-cells into either type-1 helper T-cells ($T_{H1}$ cells) or type-2 helper T-cells ($T_{H2}$ cells) as a result of the two signals. These two subtypes of $T_H$ cells and the regulatory network of cells that they selectively activate are well known to correlate with human health conditions and disease states. Differentiation into $T_{H1}$ cells results in predominantly cell-mediated immunity while differentiation into $T_{H2}$ cells results in predominantly humoral immunity. Each of these immunity types helps to protect the body against different types of invasion. Type-1 immunity protects the body against intracellular pathogens such as bacteria, but is also implicated in organ-specific autoimmune diseases. Type-2 immunity is important for protection against extracellular parasites, but is associated with allergic reactions as well. Development of $T_{H1}$ cells is driven by a cytokine called interleukin-12, which is produced by immune cells known as macrophages and dendritic cells. Interleukin-12 induces or stimulates the naive T-cell (CD4+ T-cells) to produce interferon-gamma ("IFN-gamma") and interleukin-2 ("IL-2"). These two cytokines (IL-2 and IFN-gamma) are involved in classic cell-mediated functions such as clonal expansion of cytotoxic T-lymphocytes ("CTLs"), macrophage activation, and class switching to IgG isotypes that mediate complement lysis of sensitized cells. Commitment to a $T_{H1}$ immune response is enhanced by the presence of IFN-gamma which up-regulates expression of the interleukin-12 ("IL-12") receptor while inhibiting the development of $T_{H2}$ cells. $T_{H2}$ immunity results from the production of interleukin-4 ("IL-4") by the naive T-cell. IL-4 induces $T_{H2}$ development and the subsequent production of IL-4, interleukin-5 ("IL-5"), interleukin-10 ("IL-10"), and interleukin-13 ("IL-13"). IL-4 also operates to down-regulate expression of the IL-12 receptor on developing cells, thereby inhibiting $T_{H1}$ development and helping undifferentiated T-cells to commit to $T_{H2}$ cell development. Additionally, IL-4 and IL-5 are known to activate B-cells and switch to neutralizing antibody (IgG1 in the mouse) and IgE, the initiator of immediate hypersensitivity.

Multiple sclerosis ("MS") is the disease of the central nervous systems, including brain, spinal cord, and the optic nerves because of the damage in myelin. Myelin is a fatty tissue surrounding the nerve fibers and it helps the nerve conduct the electric impulses. The lost of myelin in many nerve areas is marked by nerve damages in a form of lesions or plaques in the nervous systems called sclerosis. In some cases, the nerve fiber can also be broken. Therefore, the nerve cannot conduct the electrical impulses that are needed for the nervous system to function. As a result the MS patient shows the various symptoms of the disease, including weakness, abnormal sensation, vision changes, and clumsiness. These can be detected by abnormal responses of the pupils, weakness in arms and legs, altered reflex responses, impaired coordination, and changes in speech patterns. The damage to the nerve is due to the attack by the immune systems.

Although the cause of MS is still not clear, scientists agree that MS is one type of autoimmune diseases that is marked by inflammation and destruction of myelin. It has been found that the immune cells of MS patients have been altered. The function of suppressor T-cell decreases in the peripheral blood during acute exacerbation followed by an increase in the number of activated helper T-cells in MS patients. The number of activated T-cells that cross the blood-brain barriers into the brain is increased. These T-cells are also found in the lesion region in of the nervous systems of MS patients.

To diagnose MS is very difficult because there is no single test available to rule out and identify whether a patient has MS or not. Currently, a combination of tests is used to diagnose patients with MS, including: (a) imaging of the brain using magnetic resonance imaging ("MRI"), (b) performing Evoke potential test, and (c) evaluating materials (i.e., antibodies and proteins) found in the spinal tap fluid.

MRI provides a detailed view of the change in the brain of MS patients; this imaging tool can visualize and count the damages in the white matter in a form of lesions or plaques in brain and spinal cord. One of the indications of MS is that there are two separate demyelinating lesions, suggesting damages in the nervous system within the brain, spinal cord, and optic nerves. The observance of abnormality by MRI does not necessarily mean a development of MS because there are other diseases that can cause lesions that look similar to MS. A similar type of spots called unidentified bright spots ("UBOs") can also be found in older and healthy individuals. Thus, MRI result only cannot be used to determine occurrence of MS. On the other hand, 5% of MS patients do not show any lesions in the brain by MRI; the lesions either cannot be detected by MRI or may be found in the spinal cord. Thus, there is a need to develop a method that can specifically differentiate the presence of MS related lesions from UBOs.

The Evoke potential tests are to measure the quick and accurate the nervous system of the patient responds to a particular type of stimulation; these tests indicate the slowing down of the nerve impulse due to the destruction of myelin. Evoke potential ("EP") tests can detect the slowdown of messages carried by the nerves in various part of the brain and provides evidence of the undetected lesions by MRI. Visual Evoke Potential ("VEP") is the most common and acceptable method to diagnose MS patients.

The spinal tap is evaluated for antibodies and other marker proteins due the activation immune cells such as T-cells and B-cells. The antigen-specific activation T-cells by presentation myelin protein fragments by MHC-II molecules on the surface of APCs causes the production of antibodies and other immune-related proteins in the cerebrospinal fluids. This fluid can be sampled by a lumbar puncture or spinal tap. The presence of certain antibodies called oligoclonal bands from the spinal fluids indicates the presence of the disease and 90-95% of MS patients have oligoclonal bands. Unfortunately, these oligoclonal bands are also presence in other autoimmune diseases; thus, this test is not the only positive proof for the disease.

Because the attack of myelin is due to the activation of a subpopulation T-cells that recognize a specific antigen from proteins in myelin. The activation of antigenic-specific T-cells is due to recognition of antigens from myelin protein on the surface of APCs (i.e., B-cells, dendritic cells, and macrophages) via antigen:MHC complex. The immunological synapse is formed at the interface of T-cell:APCs via a combination of Signal-1 (TCR:MHC-peptide complexes) and Signal-2 (ICAM-1/LFA-1 complexes). Initially, the TCR:MHC-peptide complexes (Signal-1) are formed at an outer region or ring, and the ICAM-1/LFA-1 complexes (Signal-2) are formed at the inner region of the synapse. As the T-cell activation process proceeds, the ICAM-1/LFA-1 clusters migrate to the outer ring and the TCR/MHC-peptide complex moves to the inner ring. In the final state, TCR/MHC-peptide complexes congregate at the center to form a central supramolecular activation cluster ("cSMAC"), and the ICAM-1/LFA-1 complexes form a ring around the central zone to from a peripheral supramolecular activation cluster ("pSMAC").

A major goal of modern applied immunology is to be able to switch from $T_{H1}$ dominant immunity to $T_{H2}$ responses. This is especially true in autoimmune diseases like multiple sclerosis ("MS") and transplant rejection. Accordingly, what is needed in the art is modifiers of these immune responses so that type-1 immunity can be replaced with type-2 immunity as desired in order to combat different human disease states or health conditions.

In the past several years, the present inventors have conducted research in the area of bifunctional inhibitors ("BPIs"). In general, a BPI is derived from two peptides and includes a portion of a Signal-1 moiety (derived from a TCR epitope, i.e. a small peptide antigen) at one end and a portion of a Signal-2 moiety (derived from a Signal-2 receptor on the T-cell) at the other end. These two ends are directly connected to each other or connected via a non-substrate linker. The general concept of a BPI is set forth in Murray et al., U.S. Published Patent Application No. 2005/0107585, which is incorporated by reference. The work in that patent dealt largely with a BPI comprised of a GAD65 (208-217) Signal-1 moiety associated with type-1 diabetes linked to a LFA-1 alpha subunit CD11a (237-247) Signal-2 moiety.

The present invention is directed to novel BPIs and methods of use pertaining to use of the BPIs in modulating the immune response in MS and its animal model of experimental autoimmune encephalomyelitis ("EAE"), as well as a treatment and diagnostic method for MS and EAE. Moreover, the novel BPIs were capable of modulating the immune response towards a $T_{H2}$ response.

BRIEF SUMMARY OF THE INVENTION

The present invention is directed to novel bifunctional peptides useful in the treatment and/or diagnosis of EAE or MS. In one aspect, the bifunctional peptides have a first peptide portion derived from an epitope of myelin proteolipid protein, myelin oligodendrocyte glycoprotein, or oligodendrocyte-specific peptide and a second peptide portion derived from CD11a (LFA-1 alpha subunit), CD18 (LFA-1 beta subunit), CD154 (CD40L), Fas-Ligand, or CTLA4. The carboxy and/or amino termini of the bifunctional peptides may be modified. For example, in one aspect, the amino terminus is acetylated, and the carboxy terminus is amidated.

In one aspect, the peptide portions of the bifunctional peptides are preferably linked together via a linking portion. The linking portion preferably comprises at least one amino acid residue or polyethylene glycol. The linking portion may have the general formula $(A,B)_x$, wherein A and B are amino acid residues, and A amino acid residue is independently selected from the group consisting of aminocaproic acid, aminohexanoic acid, aminododecanoic acid, and β-alanine, and B amino acid residue of the linking portion is glycine, and wherein X ranges from 1 to 100.

In a preferred aspect, the bifunctional peptide comprises SEQ ID No. 86 (HSLGKWLGHPDKF-AcGAcGAc-ITDGEATDSG). Pertinent to this invention, the PLP-BPI with an antigenic sequence for MS (i.e., $PLP_{139\text{-}151}$) that is linked to $CD11a_{237\text{-}247}$ was designed to block the formation of immunological synapse by binding to APC. The selection of the antigenic peptide PLP to form PLP-BPI is based on its presentation by MHC-II. In this case, the antigenic peptide fragment (e.g., PLP) binds to MHC-II and the LFA-1 peptide fragment (e.g., LABL) binds to ICAM-1 on the surface of the APC. Because both peptides are conjugated via a linker, simultaneous binding of PLP-BPI to MHC-II and ICAM-1 prevents the translocation between TCR:MHC-II-peptide complexes (Signal-1) and ICAM-1/LFA-1 complexes (Signal-2) that forms the immunological synapse. Thus, inhibition of the immunological synapse formation selectively alters the activation of T-cells from $T_{H1}$ to $T_{H2}$ phenotypes in MS and suppresses the disease progression.

In another aspect, the bifunctional peptides are conjugated to a reporter group. The reporter group is selected from the group consisting of enzymatic groups, photochemically reactive groups, chromophoric or fluorophoric groups, luminescent groups, radioactive groups, paramagnetic ions, thermochemically reactive groups, and one part of an affinity pair. Especially preferred reporter groups are biotin or a gadolinium complex. For example, in one aspect a biotin-labeled bifunctional peptide is provided according to:

```
EbHSLGKWLGHPDKF-AcGAcGAc-      (SEQ. ID No. 90)
ITDGEATDSG
or

HSLGKWLGHPDKF-AcEbAcGAc-       (SEQ. ID No. 91)
ITDGEATDSG,
``` wherein Eb is N-γ-(N-biotinyl-3-(2-(2-(3-aminopropyloxy)-ethoxy)-ethoxy)-propyl)-L-glutamine.

In another aspect, the bifunctional peptide has a gadolinium reporter group comprised of a gadolinium complex according to:

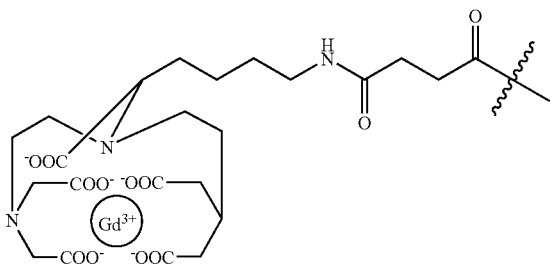

-continued

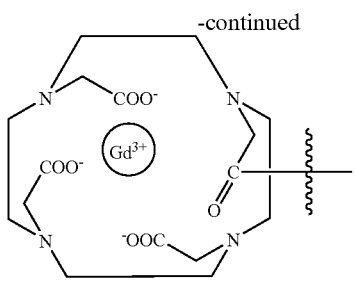

In still another aspect, the bifunctional peptides are modified to have a hydrophobic tail, for example a $C_{10}$ to $C_{30}$ hydrophobic tail. In one aspect, a compound according to:

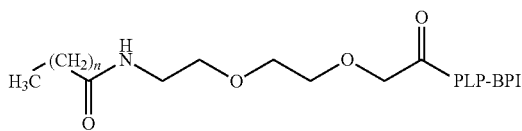

is provided, wherein n is an integer between 10 and 30, and PLP-BPI comprises a bifunctional peptide with a first peptide portion derived from an epitope of myelin proteolipid protein and a second peptide portion derived from CD11a. The hydrophobic tail may be covalently attached to the PLP-BPI via the amino terminus or via the linking portion, for example, through a lysine residue in the linking portion.

Currently, there is no available blood test for detecting MS development. Because in MS the immune response is activated, the immune cells (e.g., T-cells, B-cells, macrophages) are activated and proliferated against myelin. The number of APCs that recognize MS antigens, such as PLP, increases in the systemic circulation or localized in the lesion regions. The bifunctional peptides of the present invention (e.g. PLP-BPI) selectively bind to a specific subpopulation of APCs that cause EAE or MS. Thus, the increase of antigen specific APCs can be detected in the blood by the bifunctional peptides of the present invention (e.g. PLP-BPI).

Thus, in yet another aspect of the present invention, a method for diagnosing disease or condition associated with myelin proteolipid protein, myelin oligodendrocyte glycoprotein, or oligodendrocyte-specific peptide is provided. In one aspect, the diagnostic methods comprise administering to a subject or test sample a diagnostic composition comprising a bifunctional peptide with a reporter group attached thereto. Binding is then detected between the bifunctional peptide and antigen presenting cells in the subject or test sample, and the binding is indicative of said disease or condition. The disease or condition is preferably multiple sclerosis or experimental autoimmune encephalomyelitis.

In another aspect, the diagnostic method includes a bifunctional peptide which is conjugated to biotin, and then detecting the binding to the APC using streptavidin.

In one aspect, the diagnostic method includes a bifunctional peptide conjugated to a gamma-emitting or positron-emitting radioisotope and then detected the binding to the APC by detecting the radioisotope by camera imaging or Geiger counter.

In another aspect, the diagnostic method includes a bifunctional peptide conjugated to a paramagnetic compound and then detecting the binding to the APC by detecting the paramagnetic compound by magnetic resonance imaging. Preferred paramagnetic compounds are gadolinium.

In another aspect, the bifunctional peptide is conjugated to a reporter group by covalently attaching a hydrophobic tail to the bifunctional peptide, and inserting the bifunctional peptide into a hydrophobic region of a micelle containing the reporter group. The hydrophobic tail is preferably a $C_{10}$ to $C_{30}$ chain. In addition, the micelle containing the reporter group preferably comprises a gadolinium reporter group linked to a hydrophobic tail.

In yet a further aspect, pharmaceutical compositions comprising one or more bifunctional peptides of the present invention are provided in a pharmaceutically acceptable carrier. Methods for treating MS or EAE comprising administering those pharmaceutical compositions to a subject in need thereof are provided.

In still another aspect, a method of reducing a $T_{H1}$ immune response in EAE or MS in a subject comprising administering one or more of the bifunctional peptides of the present invention to the subject such that a $T_{h1}$ response is reduced.

In another aspect, pharmaceutical compositions comprising the BPIs of the present invention are provided. The BPIs are useful in treating MS or EAE. The BPIs are also useful in reducing a $T_H$ immune response in EAE or MS.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 8 is a comparison of the activity of PLP-BPI and controls such as a mixture of PLP and LABL peptides, and VP2-BPI.

FIG. 9 shows the effect of N-terminal and C-terminal capping on the activity of PLP-BPI and the comparison between one day and four days treatment.

DETAILED DESCRIPTION OF PREFERRED EMBODIMENT

Figure 1:
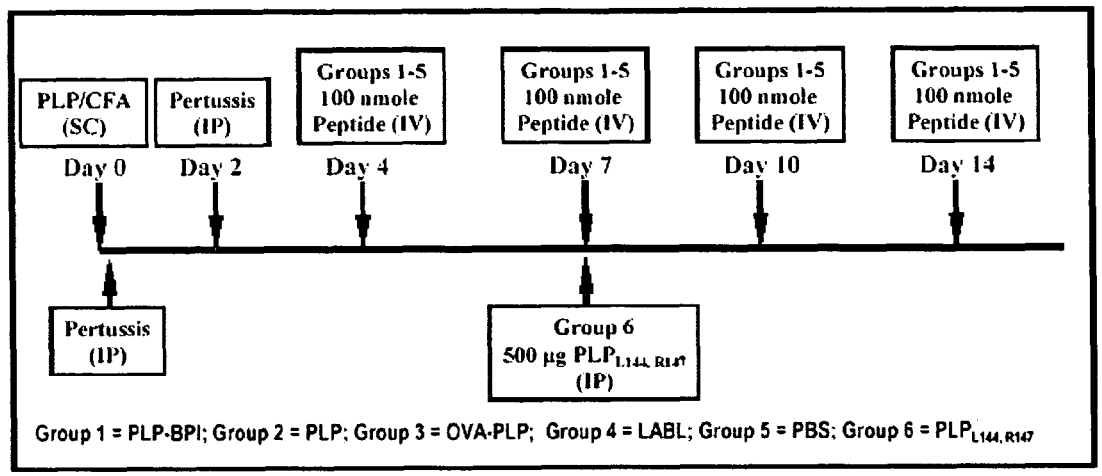
FIG. 1 shows the schedule of treatment of mice with peptides and PBS. Each group consisted of 10 mice. Groups 1-4 were treated with peptides at days 4, 7, 10, and 14. Group 5 was treated with PBS at days 4, 7, 10, and 14. Group 6 was treated with $PLP_{L144,R147}$ peptide at day 7. SC=subcutaneous; IV=intravenous; IP=intraperitoneal.

The present invention is directed to novel BPI molecules useful in the modulation of the immune response autoimmune diseases such as EAE and MS. The BPIs have a first peptide portion derived from a myelin proteolipid protein ("PLP") epitope, myelin oligodendrocyte glycoprotein ("MOG") epitope, or oligodendrocyte-specific peptide ("OSP"). The BPIs have a second peptide portion derived from CD11a (LFA-1 alpha subunit), CD18 (LFA-1 beta subunit), CD154 (CD40L), Fas-Ligand, or CTLA4. The first peptide portion and second peptide portion are preferably attached through a flexible linker. The BPIs of the present invention are useful for treating and/or diagnosing autoimmune diseases characterized by the epitopes of the BPI, such as EAE and MS.

According to another aspect, the present invention provides for pharmaceutical compositions which comprise a therapeutically effective amount of one or more BPIs of the present invention together with a pharmaceutically-acceptable carrier. The compositions may be formulated for any route of administration, in particular subcutaneous, intravenous, intraperitoneal are most preferred. The compositions may be formulated in any conventional form, for example, as tablets, capsules, caplets, solutions, suspensions, dispersions, syrups, sprays, gels, suppositories, patches, and emulsions.

In still another aspect, the present invention is directed to a method for using the PLP-PBIs of the present invention in the diagnosis of EAE or MS. The diagnostic method comprises comprising administering a subject a PLP-BPI having a reporter group conjugated thereto, and detecting binding between the PLP-BPI and an APC.

When used in a diagnostic assay, the BPI is typically labeled with a reporter group so that its binding with the APC can be detected. Any suitable reporter group well known to persons skilled in the art, including but not limited to fluorescent dyes, radioactive isotopes, enzymes which catalyze a reaction producing detectable products, biotin, or metal ions detectable by nuclear magnetic resonance can be employed.

In one embodiment, the PLP-BPIs are conjugated to a gamma-emitting or positron-emitting radioisotope and binding is detected by detecting the radioisotope by camera imaging or Geiger counter. In another embodiment, the BPI is conjugated to a paramagnetic isotope and binding is detected by detecting the paramagnetic isotope by magnetic resonance imaging ("MRI"). In still another embodiment, the BPI is conjugated to biotin, and the binding is detected by fluorescent dyes, radioactive isotope, or enzyme-streptavidin conjugates.

In another aspect, a diagnostic method in accordance with the present invention involves contacting the sample containing antigen-presenting cells (e.g., B-cells) obtained from a subject suspected of having an autoimmune disease, such as EAE or MS, with BPI of the present invention, detecting the binding of BPI to the APC in the sample, and then and determining the number of such APCs having the BPI bound thereto. The results are then compared with the number of APCs binding the BPI for a normal subject (i.e. a subject who does not have the disease). The presence of an increased number of APCs binding the BPI relative to the number of APCs in a normal subject is diagnostic for a subset of patients with the disease. In accordance with the present invention, the number of APCs that exhibit the increased binding to the BPIs may be determined either qualitatively or quantitatively.

DEFINITIONS

Unless defined otherwise, all technical and scientific terms used herein have the same meaning as commonly understood to one of ordinary skill in the art to which this invention belongs.

As used herein, the singular form "a", "an", and "the" includes plural references unless the context clearly dictates otherwise. For example, the term "a protein" includes a plurality of proteins.

As used herein, the term "detecting" embraces determining the presence, absence, or amount of a BPI in a sample (e.g. BPI being bound to an APC), and can include quantifying the amount of the binding in a sample.

As used herein, the term "derivative" or "derived from" with respect to peptides embraces changes produced by amino acid addition, deletion, replacement, substitution, and/or modification; mutants produced by recombinant and/or DNA shuffling; and salts, solvates, and other chemically synthesized/modified forms of the peptide that retain in part the activity of the isolated native peptide. Derivatives include conservative substitutions in the amino acid residue with another having similar size, charge, hydrophobicity, etc., such that the overall functionality does not change significantly.

As used herein, the term "diagnostic" embraces identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

As used herein, the term "diagnostic amount" embraces an amount of a BPI binding to APCs in a subject sample that is consistent with a particular diagnosis for a designated disease, such as MS or EAE.

As used herein, an "immunoassay" embraces an assay that uses a BPI to specifically bind an APC. Such assays are useful in the diagnosis of MS or EAE. The immunoassay is characterized by the use of specific binding properties of a particular APC to isolate, target, and/or quantify the APC. The immunoassay typically includes contacting a test sample with an APC that specifically binds the BPI, and detecting the presence of a complex of the BPI bound to the APC in the sample. The immunoassay procedure may be selected from a wide variety of immunoassay procedures known to the art directed towards antibody/antigen complexes, but which may be expanded to include BPI/APC complexes, including enzyme immunoassays, competitive or non-competitive, and including enzyme-linked immunosorbent assays ("ELISA"), radioimmunoassays ("RIA") and Western blots. Such antibody/antigen complex assays are well known to the skilled artisan and are described, for example, more thoroughly in Antibodies: A Laboratory Manual (1988) by Harlow & Lane; Immunoassays: A Practical Approach, Oxford University Press, Gosling, J. P. (ed.) (2001) and/or Current Protocols in Molecular Biology (Ausubel et al.) which is regularly and periodically updated.

As used herein, the term "MOG moiety" embraces a peptide epitope, i.e., the peptide portion of a myelin oligodendrocyte glycoprotein antigen and/or mimetics of these antigenic peptides to which important TCRs bind in MS and/or EAE.

As used herein, the term "linker" embraces a molecule that joins two other molecules together. In one aspect, the linker is any amino acid including naturally occurring or chemically synthesized amino acids. Preferably, a "linker" is a flexible, non-substrate sequence of amino acid residues resistant to proteolytic degradation which can be used to conjugate and/or couple a PLP moiety the Signal-2 moiety. Preferably, the linker is a non-substrate amino acid residue chain which helps to prevent protease attack. A particularly preferred linker is a repeating chain of the non-natural amino acid, aminocaproic acid ("Ac"), the amino acid glycine (G), and/or the amino acid lysine (Lys) (e.g. Ac-G-Ac-G-Ac or Ac-Lys-Ac-G-Aac). If a shorter length was needed for the linker, one or two pair(s) of Ac-G could be removed from the original linker, or beta-alanine residues (beta-Ala) could be substituted for one or more of the Ac residues. If a longer chain was needed for the linker, one or more pair(s) of Ac-G could be added to the original linker, or amino-dodecanoic acid residues ("Adod") could be substituted for one or more of the Ac residues. As is well known in the art, peptide mimetics of these linker amino acids may also be synthesized and inserted into the BPI structure. Other linkers include PEG-500, PEG-1000, PEG-4000.

As used herein, the term "OSP moiety" embraces a peptide epitope, i.e., the peptide portion of a myelin oligodendrocyte specific protein antigen and/or mimetics of these antigenic peptides to which important TCRs bind in MS and/or EAE.

As used herein, the phrase "pharmaceutically acceptable" embraces those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "PLP moiety" embraces a peptide epitope, i.e., the peptide portion of a myelin proteolipid protein antigen and/or mimetics of these antigenic peptides to which important TCRs bind in MS and/or EAE.

As used herein, the term "reporter group" embraces enzymatic groups, photochemically reactive groups, chromophoric or fluorophoric groups, luminescent groups, radioactive groups, paramagnetic ions, thermochemically reactive groups, and one part of an affinity pair. Examples enzymatic groups include horseradish peroxidase, alkaline phosphatase, and beta-galactosidase. Detection agents for reporter groups generally utilize a form of the enzyme's substrate. The substrate is typically modified, or provided under a set of conditions, such that a chemiluminescent, colorimetric, or fluorescent signal is observed after the enzyme and substrate has been contacted (Vargas et al., Anal. Biochem. 209: 323, 1993). Examples photochemically reactive groups include substituted coumarins, benzofurans, indols, angelicins, psoralens, carbene and nitrene precursors, ketones, and quinones, e.g., anthraquinones ("AQ"), phenanthraquinones and benzoquinonones. Examples of chromophoric and fluorophoric reporters include groups having an extensive delocalized electron system, e.g., cyanines, merocyanines, phthalocyanines, naphthalocyanines, triphenylmethanes, porphyrins, pyrilium dyes, thiapyrilium dyes, squarylium dyes, croconium dyes, azulenium dyes, indoanilines, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes, etc. Examples of suitable organic or metallated organic chromophores may be found in "Topics in Applied Chemistry: Infrared absorbing dyes" Ed. M. Matsuoka, Plenum, N.Y. 1990; "Topics in Applied Chemistry: The Chemistry and Application of Dyes", Waring et al., Plenum, N.Y., 1990; "Handbook of Fluorescent Probes and Research Chemicals" Haugland, Molecular Probes Inc, 1996; DE-A-4445065, DE-A-4326466, JP-A-3/228046, Narayanan et al. J. Org. Chem. 60: 2391-2395 (1995); Lipowska et al. Heterocyclic Comm. 1: 427-430 (1995); Fabian et al. Chem. Rev. 92: 1197 (1992); WO96/23525, Strekowska et al. J. Org. Chem. 57: 4578-4580 (1992); WO (Axis) and WO96/17628. Particular examples of chromophores and fluorophores which may be used include xylene cyanole, fluorescein, dansyl, NBD, indocyanine green, DODCI, DTDCI, DOTCI, and DDTCI. Examples of fluorescent groups include umbelliferone, fluorescein, fluorescein isothiocyanate, rhodamine, dichlorotriazinylamine fluorescein, dansyl chloride, Cy-dyes, Alexa-dyes or phycoerythrin. Examples of luminescent groups include luminol, luciferase, luciferin, and aequorin. Examples of radioactive groups are $^{125}$I, $^{131}$I, $^{35}$S or $^{3}$H. Examples of the paramagnetic groups include those containing chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Examples of thermochemically reactive groups include carboxylic acids, primary amines, secondary amines, acid hydrazides, semicarbazides, thiosemicarbazides, thiols, aliphatic hydrazines, aromatic hydrazines, epoxides and maleimides. Examples one part of an affinity pair (preferably the part having the lower molecular weight, e.g., a molecular weight of up to 7,000) includes one part of biotin/avidin, biotin/streptavidin, biotin/NeutrAvidin, glutathione/glutathione-S-transferase. Preferably, the reporter group comprises a biotin (a part of an affinity pair) or a paramagnetic ion, such as gadolinium.

As used herein, the term "sample" embraces any quantity of a substance from a subject. Such samples include, but are not limited to, blood, serum, urine, cells, organs (spleen), tissues, bone, bone marrow, lymph nodes, and skin.

As used herein, a "Signal-2 moiety" or a "Signal-2 receptor moiety" embraces a peptide portion of a second signal receptor known to bind to and/or affect binding of the receptor to its complimentary ligand on the APC. This can include peptide mimics and mimetics of the receptor/ligand structure of interest.

As used herein, a "subject" of diagnosis or treatment is a human or non-human mammal.

As used herein, a "therapeutic" treatment is a treatment administered to a subject who exhibits signs of pathology for the purpose of diminishing or eliminating those signs.

As used herein, the term "therapeutically effective dose" embraces a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding). For example, in EAE or MS, a BPI is physiologically significant if its presence results in the treatment or delay of the disease.

As used herein, "treatment" refers to prophylactic treatment or therapeutic treatment. The term "treatment" as used within the context of the present invention is meant to include therapeutic treatment as well as prophylactic, or suppressive measures for the disease or disorder. Thus, for example, the term treatment includes the administration of an BPI prior to or following the onset of a disease or disorder thereby preventing, removing, or delaying all or some signs of the disease or disorder. As another example, administration of the BPI after clinical manifestation of the disease to combat the symptoms of the disease comprises "treatment" of the disease.

BPI Synthesis

In the present invention, the BPIs were generated using automated peptide synthesis by a robotic multiple peptide synthesizer employing Fmoc amino acid chemistry by standard methods. Wang resin (p-benzyloxybenzyl alcohol polystyrene) was used as the solid support. Peptides were characterized by reversed-phase HPLC and electrospraymass-spectrometry. This synthesis, referred to as Merrifield peptide synthesis, utilizes traditional organic chemical reactions carried out on a solid material so that the peptide chain is lengthened while attached to the support structure. The peptides will be cleaved from the resin using TFA, and purified by reverse-phase HPLC and analyzed by mass spectroscopy. Alternatively, these reactions can be carried out in solution when larger amounts of the peptides are desired. Of course, the peptides of the invention may be synthesized or prepared by a number of techniques which are well known in the art. See, for example, Creighton, 1983, Proteins: Structures and Molecular Principles, W. H. Freeman and Co., New York, which is incorporated herein by reference in its entirety. Short peptides, for example, can be synthesized on a solid support or in solution. Longer peptides maybe made using recombinant DNA techniques. Here, the nucleotide sequences encoding the peptides of the invention may be synthesized, and/or cloned, and expressed according to techniques well known to those of ordinary skill in the art. See, for example, Sambrook, et al., 1989, Molecular Cloning, A is Laboratory Manual, Vols. 1-3, Cold Spring Harbor Press, New York.

Alternatively, the peptides of the invention may be synthesized such that one or more of the bonds which link the amino acid residues of the peptides are non-peptide bonds. These alternative non-peptide bonds may be formed by utilizing reactions well known to those in the art, and may include, but are not limited to amino, ester, hydrazide, semicarbazide, and azo bonds, to name but a few.

In yet another embodiment of the invention, peptides comprising the sequences described above may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the peptides' amino termini. Likewise, an acetyl group or a 9-fluorenylmethoxy-carbonyl group may be placed at the peptides' amino termini. Additionally, the hydrophobic group, t-butyloxycarbonyl, or an amido group may be added to the peptides' carboxy termini.

Pharmaceutical Compositions

The present invent is directed to a pharmaceutical composition which comprises a therapeutically effective amount of one or more BPIs of the present invention with a pharmaceutically acceptable carrier. The BPIs of the present invention may be mixed with an excipient, carrier, diluent, and optionally, a preservative or the like, pharmacologically acceptable vehicles as known in the art. Examples of excipients include glucose, mannitol, inositol, sucrose, lactose, fructose, starch, cornstarch, microcrystalline cellulose, hydroxypropylcellulose, hydroxypropyl-methylcellulose, polyvinylpyrrolidone and the like. Optionally, a thickener may be added, such as a natural gum, a cellulose derivative, an acrylic or vinyl polymer, or the like. The pharmaceutical composition including the peptide may further comprise a biodegradable polymer selected from poly-1,4-butylene succinate, poly-2,3-butylene succinate, poly-1,4-butylene fumarate and poly-2,3-butylene succinate, incorporating the peptide of the invention as the pamoate, tannate, stearate or palmitate thereof. Such compositions are known in the art as described, for example, in U.S. Pat. No. 5,439,688. The compositions for administration to humans may further comprise adjuvants that are suitable for human use, such as alum, which is approved for human use, or submicron emulsions that are intended for human use as disclosed for example in WO95/11700. Appropriate ranges of ingredients for preparing compositions with or without additional diluents, carriers or adjuvants are known in the art.

The preparation of pharmaceutical compositions comprising peptides is well known in the art, as disclosed for example in U.S. Pat. Nos. 5,736,519, 5,733,877, 5,418,219, 5,354,900, 5,298,246, 5,164,372, 4,900,549, and 4,457,917. Methods for processing the pharmaceutical compositions of the present invention include, without limitations, conventional mixing, dissolving, granulating, grinding, pulverizing, dragee-making, levigating, emulsifying, encapsulating, entrapping or lyophilizing processes.

Reporter Groups

In one aspect, the BPIs of the present invention or conjugated to a suitable reporter group. The resulting compounds are useful for diagnosing MS or EAE. Preferably, the reporter group comprises a biotin (a part of an affinity pair).

It will be appreciated from the foregoing that some of these reporter groups can be detected directly or indirectly. For example, fluorescent groups can be directly detected with a suitable detection device, such as a fluorescent microscope. Similarly, radioisotopes can be detected through the use of a scintillation counter or Geiger counter. Other reporter groups can be detected indirectly. These reporter groups may require the use of a suitable detection agent. The choice of a suitable detection agent generally depends on which detectable label is used. For example, if a protein such as biotin is used as the reporter group, a detection agent comprising avidin or streptavidin is generally employed (Bayer et al., Meth. Biochem. Anal. 26: 1-10, 1980).

In the context of MRI, complexes of the reporter groups (e.g. paramagnetic contrast agents) are especially preferred for attachment to the BPI. For example, many currently used well-known paramagnetic agents include ferric ammonium citrate, gadolinium-DTPA, chromium-DTPA, chromium-EDTA, manganese-DTPA, manganese-EDTA, manganese chloride, iron sulfate and mixtures thereof. Exemplary contrast agents that are complexed with various chelating agents are disclosed in Brechbiel, U.S. Pat. No. 6,852,842. Of these, gadolinium complexes are most preferred. See Rudovski et al., *Synthesis of a bifunctional monophosphinic acid DOTA analogue ligand and its lanthanide(III) complexes. A gadolinium(III) complex endowed with an optimal water exchange rate for MRI applications*, Org Biomol Chem. Jan. 7, 2005; 3(1):112-7; Langereis et al., *Probing the interaction of the biotin-avidin complex with the relaxivity of biotinylated Gd-DTPA*, Org Biomol Chem. May 7, 2004; 2(9):1271-73; Fulton et al., *Efficient relaxivity enhancement in dendritic gadolinium complexes: effective motional coupling in medium molecular weight conjugates*, Chem Commun (Camb). Jan. 28, 2005; (4):474-76; Whetstone et al., *Element-coded affinity tags for peptides and proteins*, Bioconjug Chem. January-February 2004; 15(1):3-6; Anelli et al., *Conjugates of gadolinium complexes to bile acids as hepatocyte-directed contrast agents for magnetic resonance imaging*, J Med Chem. Jul. 1, 2004; 47(14):3629-41; Frullano et al., *Towards targeted MRI: new MRI contrast agents for sialic acid detection*, Chemistry, Oct. 11, 2004; 10(20):5205-17; Lebduskova et al., *A gadolinium(III) complex of a carboxylic-phosphorus acid derivative of diethylenetriamine covalently bound to inulin, a potential macromolecular MRI contrast agent*, Bioconjug Chem. July-August 2004; 15(4):881-9; Laurent et al., *Synthesis and physicochemical characterization of Gd-DTPA-B(sLex)A, a new MRI contrast agent targeted to inflammation*, Bioconjug Chem. January-February 2004; 15(1):99-103; Arceuil et al., *An MRA study of vascular stenosis in a pig model using CH3-DTPA-Gd (NMS60) and Gd-DTPA*, Magn Reson Imaging. November 2004; 22(9):1243-8; Woods et al., *Synthesis, relaxometric and photophysical properties of a new pH-responsive MRI contrast agent: the effect of other ligating groups on dissociation of a p-nitrophenolic pendant arm*, J Am Chem Soc. Aug. 4, 2004; 126(30): 9248-56; Aime et al., *[Gd-AAZTA]-: a new structural entry for an improved generation of MRI contrast agents*, Inorg Chem. Nov. 29, 2004; 43(24):7588-90, which are incorporated by reference.

In one aspect of the present invention, the contrast agent is directly conjugated to the BPI by forming a covalent bond between the BPI and the chelating portion of the paramagnetic agent complex.

In another aspect, the contrast agent is indirectly conjugated to the BPI by incorporating both into a micelle. For example, the amino-terminus of the BPI may be modified to have a long hydrophobic tail that will be inserted into the hydrophobic region of the micelle. For example, the BPIs of the present invention may be modified according to the formula:

wherein n is an integer between 10 and 30.

The BPIs of the present invention may be linked to the long hydrophobic region at the amino terminus or the linker of the BPI itself (e.g. a lysine residue in the linker).

The paramagnetic complex is similarly modified to include a long hydrophobic tail that will also be inserted into the hydrophobic region of the micelle. For example, a preferred gadolinium complex having a hydrophobic tail is according to the formula:

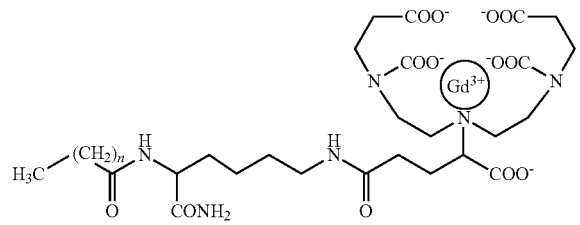

wherein n is an integer between 10 and 30.

The BPIs may also be conjugated to the contrast agent via a polymeric particle. The particle is preferably a nanoparticle (i.e. a particle having an average particle size less than about 1000 nm), but larger particles may also be used. Suitable polymeric biomaterials include such as poly(DL-lactide-co-glycolide) (PLG), polylactic acid (PLA), or poly(lactic-co-glycolic acid) (PLGA). The contrast agent (Gd, iron oxide, and the like) is absorbed, doped or loaded onto the polymeric particle. See Faranesh et al., *In vitro release of vascular endothelial growth factor from gadolinium-doped biodegradable microspheres*, Magn Reson Med. June 2004; 51(6):1265-71; Berkland et al., *Fabrication of PLG microspheres with precisely controlled and monodisperse size distributions*, J Control Release May 18; 73(1):59-74 (2001), Zhu et al., *Biocompatible nanotemplate-engineered nanoparticles containing gadolinium: stability and relativity of a potential MRI contrast agent*, J Nanosci Nanotechnol. April 2006; 6(4):996-1003; Anderson et al., *Magnetic resonance imaging of labeled T-cells in a mouse model of multiple sclerosis*, Ann. Neurol. May 2004; 55(5):654-9, which are incorporated by reference. The BPI may be covalently attached to the polymer forming the polymeric particle, e.g. PLGA, as set forth below:

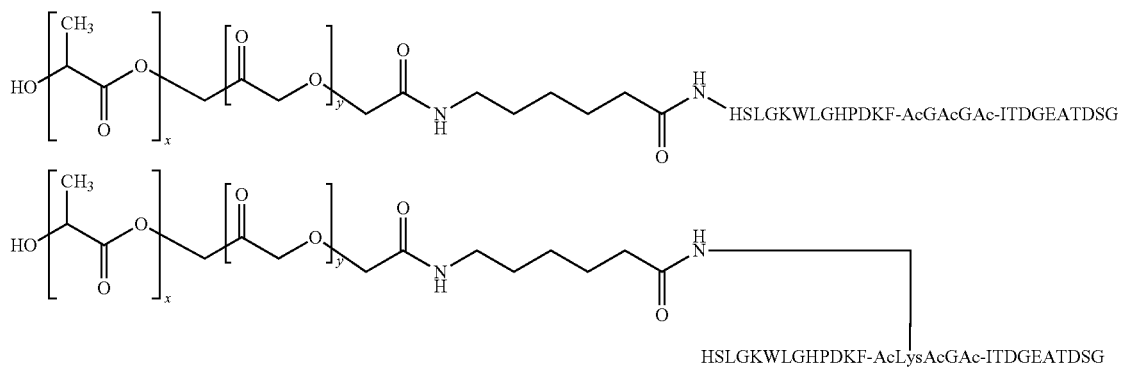

wherein X and Y are independently integers between 10 and 10,0000.

Animal Models

Throughout the present specification, reference is made to various model systems that have been developed for studying autoimmune diseases. EAE has been studied in mice and other mammalian species as a model for MS. Those of ordinary skill in the art recognize that virtually all potential immune therapies for MS are first tested in this animal model system. The disease is induced by parenteral administration of MBP or PLP or myelin oligodendrocyte glycoprotein ("MOG"), or peptides derived from those proteins and an adjuvant (such as Freund's Complete Adjuvant, FCA). This treatment, with either antigen, induces both a monophasic and an exacerbating/remitting form of demyelinating disease (depending on the species and details of administration). The induced disease has the characteristics of the autoimmune disease MS.

The following examples set forth exemplary embodiments of the present invention. It is to be understood, however, that these examples are provided by way of illustration and nothing therein should be taken as a limitation upon the overall scope of the invention.

Example 1

Synthesis of PLP-BPI

In this example, an exemplary PLP-BPI having the sequence HSLGKWLGHPDKF-AcGAcGAc-ITDGEATDSG (SEQ. ID NO. 86) was prepared. In general, the PLP-BPI comprises an antigenic PLP sequence for MS (e.g., $PLP_{139-151}$, SEQ ID NO. 2) that is linked to the a peptide from CD 11a (e.g. $CD11a_{237-247}$ (SEQ ID NO. 49)). The selection of the antigenic peptide PLP to form PLP-BPI is based on its presentation by MHC-II (e.g., I-$A^s$ for SJL/J mice). A complex between PLP and I-$A^s$ on APC is presented to TCR on the surface of a subpopulation of T-cells for their activation.

It will be appreciated additional BPIs for MS may be prepared using other antigenic peptide sequences for EAE and/or MS. In particular, the "Signal-1" moiety may comprise various epitopes derives from PLP, myelin oligodendrocyte glycoprotein ("MOG") peptides, oligodendrocyte-specific protein ("OSP"). Some suitable epitopes for forming the BPIs of the present invention are provided in Table 1.

TABLE 1

Signal-1 Peptides for PBIs

| SEQ ID NO | PLP/MOG/OSP Moiety Sequence | Organism | Sequence |
|---|---|---|---|
| 1 | PLP 139-151 | Homo sapiens | HCLGKWLGHPDKF |
| 2 | PLP 139-151 | Homo sapiens | HSLGKWLGHPDKF Note: C > S mutation |
| 3 | PLP 139-151 | Homo sapiens | HSLGKQLGHPDKF Note: C > S, W > Q mutation |
| 4 | PLP 139-151 | Homo sapiens | HSLGKLLGRPDKF Note: C > S, W > L, H > R mutation |
| 5 | PLP 139-151 | Homo sapiens | HSLGKWDGHPDKF Note: C > S, L > D mutation |
| 6 | PLP 40-60 | Homo sapiens | LTGTEKLIETYFSKNYQDYEY |
| 7 | PLP 89-106 | Homo sapiens | EGFYTTGAVRQIFGDYKT |
| 8 | PLP 25-56 | Homo sapiens | CFFGVALFCGCGHEALTGTEKLIETYFSKNYQ |
| 9 | PLP 217-248 | Homo sapiens | GKVCGSNLLSICKTAEFQMTFHLFIAAFVGAA |
| 10 | PLP 257-276 | Homo sapiens | FMIAATYNFAVLKLMGRGTK |
| 11 | PLP 91-110 | Homo sapiens | FYTTGAVRQIFGDYKTTICG |
| 12 | PLP 43-64 | Homo sapiens | TEKLIETYFSKNYQDYEYLINV |
| 13 | PLP 104-117 | Homo sapiens | KTTICGKGLSATVT |
| 14 | PLP 56-70 | Homo sapiens | DYEYLINVIHAFQYV |
| 15 | PLP 178-191 | Homo sapiens | NTWTTCQSIAFPSK |
| 16 | MOG 8-21 | Homo sapiens | PGYPIRALVGDEAE |
| 17 | MOG 35-55 | Rat, mouse | MEVGWYRSPFSRVVHLYRNGK |

TABLE 1-continued

Signal-1 Peptides for PBIs

| SEQ ID NO | PLP/MOG/ OSP Moiety Sequence | Organism | Sequence |
|---|---|---|---|
| 18 | MOG 97-108 | Homo sapiens | TCFFRDHSYQEE |
| 19 | OSP 12-31 | Homo sapiens | VTSFVGWIGVIVTTSTNDWV |
| 20 | OSP 22-41 | Homo sapiens | IVTTSTNDWVVTCGYTIPTC |
| 21 | OSP 32-51 | Homo sapiens | VTCGYTIPTCRKLDELGSKG |
| 22 | OSP 42-61 | Homo sapiens | RKLDELGSKGLWADCVMATG |
| 23 | OSP 52-71 | Homo sapiens | LWADCVMATGLYHCKPLVDI |
| 24 | OSP 62-81 | Homo sapiens | LYHCKPLVDILILPGYVQAC |
| 25 | OSP 72-91 | Homo sapiens | LILPGYVQACRALMIAASVL |
| 26 | OSP 82-101 | Homo sapiens | RALMIAASVLGLPAILLLLT |
| 27 | OSP 92-111 | Homo sapiens | GLPAILLLLTVLPCIRMGQE |
| 28 | OSP 102-121 | Homo sapiens | VLPCIRMGQEPGVAKYRRAQ |
| 29 | OSP 112-131 | Homo sapiens | PGVAKYRRAQLAGVLLILLA |
| 30 | OSP 132-151 | Homo sapiens | LCALVATIWFPVCAHRETTI |
| 31 | OSP 152-171 | Homo sapiens | VSFGYSLYAGWIGAVLCLVG |
| 32 | OSP 162-181 | Homo sapiens | WIGAVLCLVGGCVILCCAGD |
| 33 | OSP 172-191 | Homo sapiens | GCVILCCAGDAQAFGENVST |
| 34 | OSP 182-201 | Homo sapiens | AQAFGENVSTTLRALAPRLM |
| 35 | OSP 192-211 | Homo sapiens | TLRALAPRLMRRVPTYKRAA |
| 36 | OSP 202-218 | Homo sapiens | RRVPTYKRAARLPTEVE |
| 37 | OSP 12-25 | Mus musculus | VTSFVGWIGIIVTTSTNDWV |
| 38 | OSP 22-41 | Mus musculus | IVTTSTNDWVVTCSYTIPTC |
| 39 | OSP 32-51 | Mus musculus | VTCSYTIPTCRKMDELGSKG |
| 40 | OSP 42-61 | Mus musculus | RKMDELGSKGLWADCVMATG |
| 41 | OSP 92-111 | Mus musculus | GLPAILLLLTVLPCIRMGHE |
| 42 | OSP 102-121 | Mus musculus | VLPCIRMGHEPGVAKYRRAQ |
| 43 | OSP 132-151 | Mus musculus | LCAIVATIWFPVCAHREITI |
| 44 | OSP 142-161 | Mus musculus | PVCAHREITIVSFGYSLYAG |
| 45 | OSP 172-191 | Mus musculus | GCVIVCCSGDAQSFGENRFY |
| 46 | OSP 182-201 | Mus musculus | AQSFGENRFYYSSGSSSPTH |
| 47 | OSP 192-207 | Mus musculus | YYSSGSSSPTHAKSAHV |

The Signal-1 moieties may be combined with other Signal-2 peptide portions. In particular, peptides associated with the alpha subunit of LFA-1 (CD11a) or the beta subunit of LFA-1 (CD18) may be suitable for forming BPIs of the present invention. Other Signal-2 moieties are those derived from CTLA4, CD154 (CD40L), and Fas-Ligand as provided in Table 2.

TABLE 2

Signal-2 Peptide Moieties

| SEQ ID NO. | Peptide | Organism | Peptide Sequence |
|---|---|---|---|
| 48 | CD11a LFA-1 α-subunit 237-261 | Homo sapiens | ITDGEATDSGNIDAAKDII-YIIGI (Note: dash is a deleted residue from the original sequence of CD11a) |
| 49 | CD11a LFA-1 α-subunit 237-246 | Homo sapiens | ITDGEATDSG |
| 50 | CD11a LFA-1 α-subunit 238-248 | Homo sapiens | TDGEATDSGN |
| 51 | CD11a LFA-1 α-subunit 237-246 | Homo sapiens | Cyclo(1, 12)PenITDGEATDSGC (Note: Pen and Cys residues were added to the N- and C-terminus for forming a disulfide bond between Pen1 to Cys 12) |
| 52 | CD11a LFA-1 α-subunit 237-242 | Homo sapiens | ITDGEA |
| 53 | CD11a LFA-1 α-subunit 238-243 | Homo sapiens | TDGEAT |
| 54 | CD11a LFA-1 α-subunit 239-244 | Homo sapiens | DGEATD |

TABLE 2-continued

Signal-2 Peptide Moieties

| SEQ ID NO. | Peptide | Organism | Peptide Sequence |
|---|---|---|---|
| 55 | CD11a LFA-1 α-subunit 240-245 | Homo sapiens | GEATDS |
| 56 | CD11a LFA-1 α-subunit 241-246 | Homo sapiens | EATDSG |
| 57 | CD11a LFA-1 α-subunit 237-242 | Homo sapiens | Cyclo(1, 6)ITDGEA (Note: N- to C-terminal cyclization) |
| 58 | CD11a LFA-1 α-subunit 237-242 | Homo sapiens | Cyclo(1, 6)ITDGEK (Note: N- to C-terminal cyclization with K mutation at residue 6) |
| 59 | CD11a LFA-1 α-subunit 244-253 | Homo sapiens | DSGNIDAAKD |
| 60 | CD11a LFA-1 α-subunit 244-253 | Homo sapiens | Cyclo(1, 12)PenDSGNIDAAKDC (Note: Pen and Cys residues were added to the N- and C-terminus for forming a di-sulfide bond between Pen1 to Cys12) |
| 61 | CD11a LFA-1 α-subunit 251-261 | Homo sapiens | AKDII-YIIGI |
| 62 | CD11a LFA-1 α-subunit 251-261 | Homo sapiens | Cyclo(1, 12)PenAKDII-YIIGIC (Note: Pen and Cys residues were added to the N- and C-terminus for forming a di-sulfide bond between Pen1 to Cys 12) (Note: dash is a deleted residue from the original sequence of CD11a) |
| 63 | CD11a LFA-1 α-subunit 441-465 | Homo sapiens | GVDVDQDGETEL-IGAPLFYGEQRG (Note: dash is a deleted residue from the original sequence of CD11a) |
| 64 | CD11a LFA-1 α-subunit 441-450 | Homo sapiens | GVDVDQDGET |
| 65 | CD11a LFA-1 α-subunit 441-450 | Homo sapiens | Cyclo(1, 12)PenGVDVDQDGETC |
| 66 | CD11a LFA-1 α-subunit 448-458 | Homo sapiens | PenGETEL-IGAPL (Note: dash is a deleted residue from the original sequence of CD11a) |
| 67 | CD11a LFA-1 α-subunit 448-458 | Homo sapiens | Cyclo(1, 12)PenGETEL-IGAPLC (Note: dash is a deleted residue from the original sequence of CD11a) |
| 68 | CD11a LFA-1 α-subunit 456-465 | Homo sapiens | APLFYGEQRG |
| 69 | CD11a LFA-1 α-subunit 456-465 | Homo sapiens | Cyclo(1, 12)PenAPLFYGEQRGC |
| 70 | CD18 LFA-1 β-subunit 112-137 | Homo sapiens | DLSYS-LDDLRNVKKLGGDLLRALNE (Note: dash is a deleted residue from the original sequence of CD11a) |
| 71 | CD18 LFA-1 β-subunit 112-122 | Homo sapiens | DLSYS-LDDLR (Note: dash is a deleted residue from the original sequence of CD11a) |
| 72 | CD18 LFA-1 β-subunit 112-122 | Homo sapiens | Cyclo(1, 12)PenDLSYS-LDDLRC (Note: dash is a deleted residue from the original sequence of CD11a) |
| 73 | CD18 LFA-1 β-subunit 120-129 | Homo sapiens | DLRNVKKLGG |
| 74 | CD18 LFA-1 β-subunit 120-129 | Homo sapiens | Cyclo(1, 12)PenDLRNVKKLGGC |
| 75 | CD18 LFA-1 β-subunit 128-137 | Homo sapiens | GGDLLRALNE |
| 76 | CD18 LFA-1 β-subunit 128-137 | Homo sapiens | Cyclo(1, 12)PenGGDLLRALNEC |
| 77 | CTLA4 24-33 | Homo sapiens | ASPGKATEVR |
| 78 | CTLA4 24-33 | Mus musculus | SPSHNTDEVR |
| 79 | CTLA4 93-104 | Homo sapiens | KVELMYPPPYYL |
| 80 | CTLA4 93-104 | Mus musculus | KVELMYPPPYFV |
| 81 | CD11a 237-247 | Mus musculus | ITDGEATDSG |
| 82 | CD154 (CD40L) 93-104 | Homo sapiens | KGYYTMSNNLVTL |
| 83 | CD154 (CD40L) 93-104 | Mus musculus | KGYYTMSNNLVTL |
| 84 | Fas-ligand (CD95L) 143-155 | Homo sapiens | YMRNSKYRAGGAYGPG |

TABLE 2-continued

Signal-2 Peptide Moieties

| SEQ ID NO. | Peptide | Organism | Peptide Sequence |
|---|---|---|---|
| 85 | Fas-ligand (CD95L) 143-155 | Mus musculus | YMRNSKYRAGGAYGPG |

Example 2

Neuroprotection

In this example, PLP-BPI was evaluated in the EAE mouse model for MS. First, the efficacy of PLP-BPI was investigated in comparison to PLP peptide ($PLP_{139-151}$), $PLP_{L,R}$, and other negative controls (OVA-BPI and LABL) in the EAE animal model. The sequences of these synthetic peptides are set forth as follows.

TABLE 3

Name and sequence of peptides in in vivo EAE experiments.

| SEQ ID NO. | Peptide Name | Origin | Sequence |
|---|---|---|---|
| 86 | PLP-BPI | $PLP_{139-151}$-Link.-LABL | HSLGKWLGHPDKF-AcGAcGAc-ITDGEATDSG |
| 87 | OVA-BPI | $Oval_{328-339}$-Link.-LABL | AVHAAHAEINEA-AcGAcGAc-ITDGEATDSG |
| 49 | LABL | $CD11a_{237-247}$ | ITDGEATDSG |
| 2 | PLP | $PLP_{139-151}$ | HSLGKWLGHPDKF |
| 4 | $PLP_{L,R}$ | $PLP_{L144,R147}$ (mutant) | HSLGKLLGRPDKF |
| 88 | Ac-PLP-BPI-NH$_2$ | Capped PLP-BPI | Ac-HSLGKWLGHPDKF)-AcGAcGAc-ITDGEATDSG-NH$_2$ |
| 89 | VP2-BPI | $VP2_{74-86}$-Link.-LABL | QEAFSHIRIPLPH-AcGAcGAc-ITDGEATDSG |

As mentioned above, PLP-BPI contains a sequence of $PLP_{139-151}$, that is linked to LABL peptide from CD11a of LFA-1. The PLP fragment binds to I-A$^s$ (Signal-1) and the LABL fragment binds to ICAM-1 (Signal-2) on the surface of APC. Thus, treatment of EAE mice with PLP-BPI suppresses the activation of a subpopulation of T-cells that recognize a complex between PLP-BPI to I-A$^s$ and ICAM-1. As a positive control, $PLP_{139-151}$ and $PLP_{L,R}$ were used to suppress EAE progression. OVA-LABL and LABL peptides were used as negative controls. OVA-BPI contains a sequence of ovalbumin that is not recognized by I-A$^s$; however, LABL peptide fragment is recognized by ICAM-1. LABL peptide alone was also used to test whether blocking only Signal-2 (cell adhesion signal) is sufficient to suppress EAE. Finally, $PLP_{L,R}$ with mutation at residues 144 ($W_{144} \rightarrow L_{144}$) and 147 ($H_{147} \rightarrow R_{147}$) was also used as another control.

To evaluate the in vivo activity of these molecules, SJL/J female mice at 6-8 weeks of age (Jackson Laboratory, Bar Harbor, Me.) were divided into six groups with ten mice in each group. The treatment schedule of mice is shown in FIG. 1. At the initiation state (Day 0), all mice (10/group) were immunized by subcutaneous (s.c.) inoculation with 200 µg of PLP in a 0.2 mL emulsion with equal volumes of phosphate buffered saline ("PBS") and complete Freund's adjuvant ("CFA") (Difco, Detroit, Mich.). To enhance immunization with antigen, killed Mycobacterium tuberculosis strain H37RA (Difco) was added to the emulsion at a concentration of 4 mg/mL and administered to regions above the shoulder and the flanks. The injection volume was 50 µL at each injection site. In addition, 200 ng of pertussis toxin (List Biological Laboratories, Campbell, Calif.) was injected intraperitoneally (i.p.) on the day of immunization and 48 hours post-immunization. The onset of disease was on day 8 to day 12 post-immunization. Then, each mouse in Groups 1-4 received intravenous (i.v.) injections of 100 nmole/100 µL of the test peptides (PLP-BPI, $PLP_{139-151}$, OVA-BPI, LABL) on days 4, 7, 10 and 14. Group 5 animals were injected with PBS on days 4, 7, 10 and 14. Group 6 animals received one i.p. injection of 500 µg $PLP_{L,R}$ on day 7.

Disease progression was evaluated using a clinical scoring scale ranging from 0 to 5 as shown in Table 4:

TABLE 4

The score of disease progression in the mouse EAE model

| Score | Gross Pathology |
|---|---|
| 0 | No clinical disease |
| 1 | Tail weakness |
| 2 | Paraparesis (weakness, incomplete paralysis of one or two hind limbs) |
| 3 | Paraplegia (complete paralysis of two hind limbs) |
| 4 | Paraplegia with forelimb weakness or paralysis |
| 5 | Moribund or death |

All of the immunized mice were scored blindly 5-6 days/week by the same observer. Mean daily clinical scores were calculated by adding the grades of each mouse individually divided by the number of mice in each group. All animals were observed daily and, upon signs of paralysis and weakness, gel food and Napa nectar were provided to the animals to prevent dehydration. Saline was injected (s.c.) if a weight loss of 10% was observed within a 24-hour period. Body weight and disease scoring started at the onset of the disease (day 8). The measurements were continued daily (5 to 6 days/week) until the end of the disease.

Figure 2:
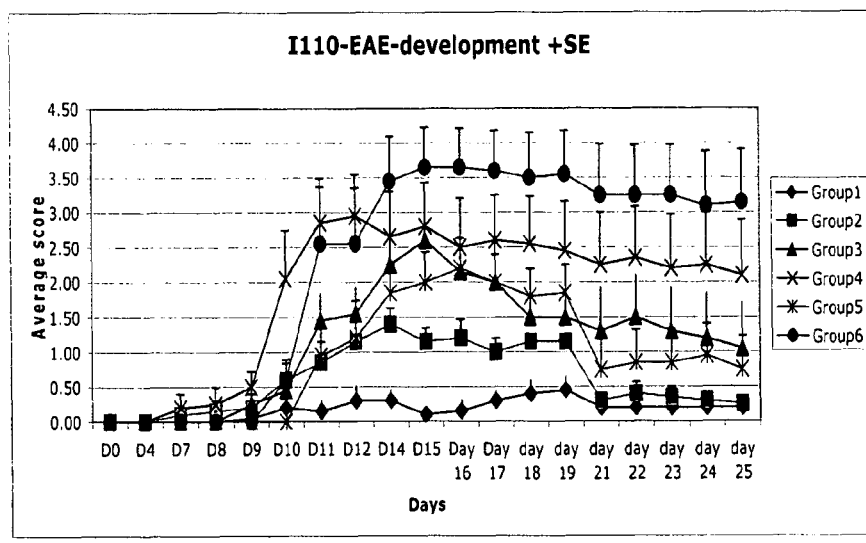
FIG. 2 shows the effect of PLP-BPI in suppressing EAE in female SJL/J mice. EAE was induced by 200 µg PLP in a 0.2 mL emulsion with equal volumes of PBS and CFA at day 0. 100 nmol/mouse of peptides such as PLP-BPI (Group 1), $PLP_{139-151}$ alone (Group 2), OVA-BPI (Group 3; control), LABL peptide (Group 4, control), PBS (Group 5, control), and $PLP_{L,R}$ (Group 6, control) were injected at days 4, 7, 10 and 14 to challenge the progression of EAE.
Figure 3:
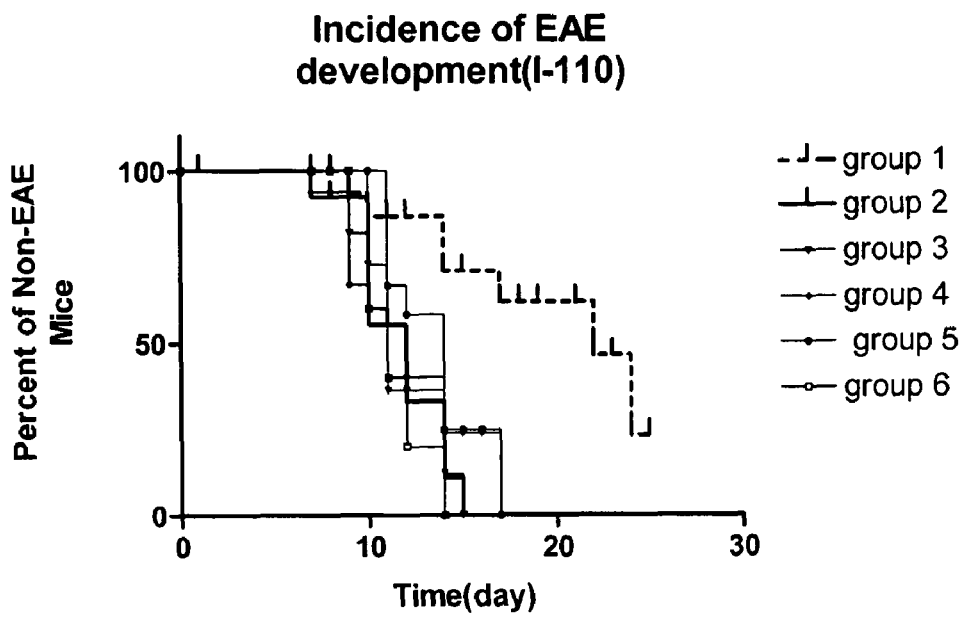
FIG. 3 shows the EAE-incidence in mice treated with peptides (Groups 1-4 and 6) compared to control (PBS; Group 5). Group 1 (PLP-BPI), Group 2 ($PLP_{139-151}$ peptide), Group 3 (OVA-BPI) Group 4 (LABL peptide), Group 5 (PBS), and Group 6 ($PLP_{L,R}$ peptide)

The effect of PLP-BPI compared to that of control peptides or PBS in the EAE mouse model was evaluated (FIGS. 2 and 3). The mice treated with PLP-BPI (Group 1) had a significantly lower EAE score than the control group (Group 5, PBS) as well as the PLP-treated mice. Although PLP (Group 2) had a better efficacy than PBS or control peptides, PLP-BPI suppressed the EAE progression better than $PLP_{139-151}$ alone (FIG. 2); the daily score of PLP-BPI-treated mice is very low throughout the entire study compared to that of $PLP_{131-51}$-treated mice. Furthermore, the PLP-BPI-treated mice had a lower EAE-incidence than did control (Group 5) and other peptide-treated mice (Groups 2, 3, 4, 6) (FIG. 3). Mice treated with OVA-BPI (Group 3) and LABL (Group 4) peptide had a disease progression similar to that of the control group (Group 5) (FIG. 2). $PLP_{L,R}$-treated mice (Group 6) had the worst EAE scores and incidence.

The statistical analyses of the EAE scores and EAE incidence were done using Mann-Whitney U test and Kaplan-Meier analysis, respectively. The comparison was done between the peptide-treated mice (Groups 1, 2, 3, 4, and 6)

and the control group (Group 5) at day 14 post-immunization. On day 14, EAE scores of Group 1 (PLP-BPI) were significantly lower than those of controls (Group 5). In the whole experiment, Group 1 (PLP-BPI) had a significantly lower EAE incidence than did control Group 5. On the other hand, the EAE incidence of Group 6 ($PLP_{L,R}$) was significantly higher than that of controls. In conclusion, the results suggest that PLP-BPI can significantly inhibit the disease progression; in addition, it lowers the incidence of EAE development in mice.

TABLE 5

Statistical analyses of EAE scores and EAE incidence

| EAE Score | Mann-Whitney U test p values vs. Group 5 | Kaplan-Meier Analysis p values vs. Group 5 |
|---|---|---|
| Group 1 (PLP-BPI) | 0.002* | 0.013* |
| Group 2 ($PLP_{139-151}$) | 0.50 | 0.06 |
| Group 3 (LABL) | 0.65 | 0.07 |
| Group 4 (LABL) | 0.79 | 0.26 |
| Group 6 ($PLP_{L,R}$) | 0.16 | 0.02* |

*= p < 0.05

Figure 4:
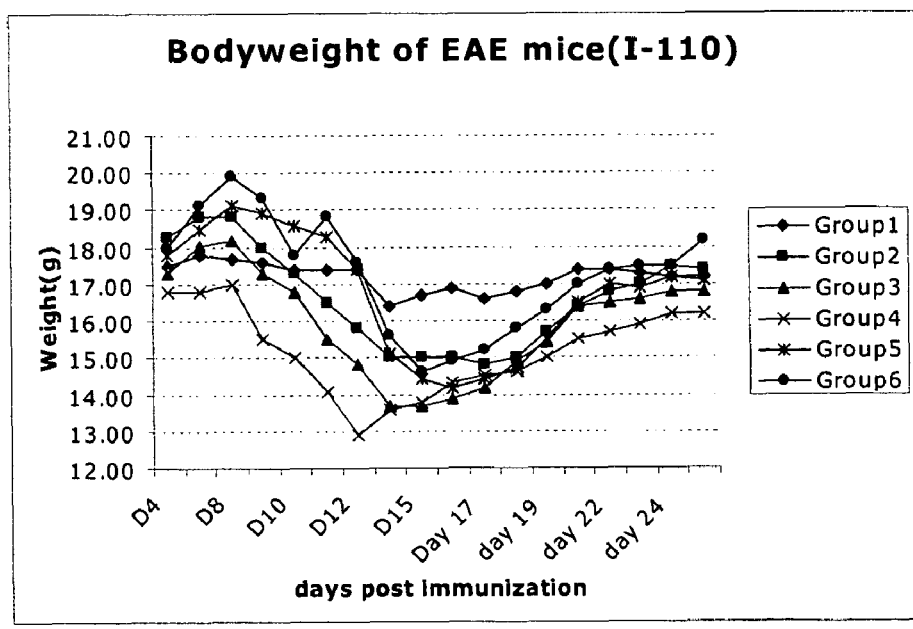
FIG. 4 shows the average body weights of animals in each group during the experiment. Group 1 (PLP-BPI), Group 2 ($PLP_{139-151}$ peptide), Group 3 (OVA-BPI) Group 4 (LABL peptide), Group 5 (PBS), and Group 6 ($PLP_{L,R}$ peptide).

Body weight loss was observed after the EAE onset, starting on day 7 (FIG. 4). On day 15, the loss of weight in PLP-BPI-treated mice was only about 10% compared to 24% in control Group 5. The PLP-BPI-treated mice (Group 1) had the lowest weight fluctuation compared to other groups in this study. All the groups recovered their body weights after day 20 and maintained their weights.

The mortality of the animals was also monitored (Table 6). It is interesting to find that no animals died in Group 1 (PLP-BPI) and Group 2 (PLP). On the other hand, $PLP_{L,R}$-treated mice tended toward worsening of the EAE disease (Group 6), and a total of six out of ten animals in this group died on day 11 (5 animals) and day 14 (1 animal). This suggests that this molecule had a severe effect (toxicity) on the animals. The LABL-treated mice (Group 4) had the second highest mortality rate (four out of ten). It is not clear whether this peptide is toxic or has a specific mechanism in regulating leukocyte adhesion that affects the immune response. One animal in the control group (Group 5) treated with PBS died. These results suggest that PLP-BPI prevents the progression of EAE and has low toxicity.

TABLE 6

The number and the identity of the animals that died during this experiment.

| | Day 10 | Day 11 | Day 14 | Total |
|---|---|---|---|---|
| Group 1 (PLP-BPI) | 0 | 0 | 0 | 0 |
| Group 2 ($PLP_{139-151}$) | 0 | 0 | 0 | 0 |
| Group 3 (OVA-BPI) | 0 | 0 | 2 | 2 |
| Group 4 (LABL) | 3 | 1 | 0 | 4 |
| Group 5 (PBS) | 0 | 1 | 0 | 1 |
| Group 6 ($PLP_{L,R}$) | 0 | 5 | 1 | 6 |

Example 3

Modulation of Immune Response using PLP-BPI

To elucidate the mechanism of action of PLP-BPI and its effect on T-cell commitment, we investigated the presence of cytokine-producing T-cells on EAE mice treated with PLP-BPI and PBS. Similar to Example 2, the experiments were repeated with two groups of mice (12 mice in each group). These mice were injected with PLP peptide in CFA at day 0 followed by injection of pertussis toxin on day 0 and day 2 to induce EAE. Then, Group 1 animals received 100 µL of PBS (i.v.) as a control and Group 2 mice received i.v. injections of 100 nmol/100 µL of PLP-BPI on days 4, 7, 10 and 14. The progression of EAE disease severity (scores) and animal body weights were recorded daily until day 25. At day 15, six mice from each group were sacrificed for evaluation of cytokine-producing T-cells. After day 25, the rest of the mice were followed twice a week up to day 43 for EAE relapse.

Figure 5:
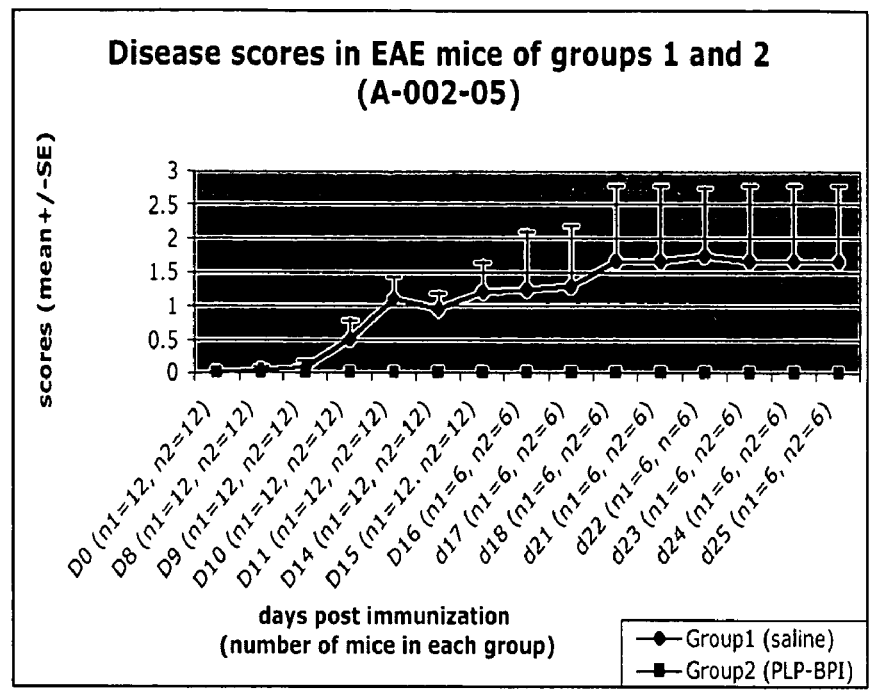
FIG. 5 shows the disease scores in a study to evaluate the mechanism of T-cell commitment after treating with PLP-BPI (Group 2) and PBS (Group 1). n1 or n2=12 up to day 15. n1 or n2=6 from day 16 to day 25. (Mann-Whitney U test, p=0.0031; Kaplan-Meier analysis, p=0.0129)

As in the previous example, PLP-BPI-treated mice (Group 2) did not have any symptoms of EAE up to day 25 (FIG. 5). In contrast, PBS-treated mice (Group 1) began to show EAE symptoms at day 8, and all mice showed EAE at day 14, which continued up to day 25 (FIG. 5). The number of mice changed in each group after day 15 because half of the animals were used for the in vitro studies to evaluate the cytokine-producing T-cells. The EAE severity in Group 2 (PLP-BPI treated) was significantly lower than that in Group 1 (PBS, control) (p=0.0031 using Mann-Whitney U test and p=0.0129 using Kaplan-Meier analysis). Around days 25 to 28, the surviving mice in Group 1 recovered from EAE; however, EAE relapse occurred beginning on day 32 with an increasing score up to day 43 (data not shown). In contrast, no EAE relapse was observed in PLP-BPI-treated mice (Group 2). Group 1 showed body weight loss beginning on day 9 with the maximum weight loss reaching approximately 20% on day 14; however, mice in Group 2 showed no significant loss of body weight (data not shown). All mice in Group 1 recovered their body weight after day 20 and maintained their weights.

To determine the effect of PLP-BPI in altering the behavior of T-cells, the cytokine-producing T-cells from Group 1 and Group 2 was compared. When 50% of the animals in the control group (Group 1) showed sign of disease but not before the treatment course in Group 2 was completed at day 14, six animals/group whose scores were closest to the mean scores were sacrificed, and cells from the spleen, draining inguinal, and popliteal lymph nodes were harvested. These cells were stimulated in vitro with mitomycin and PLP-peptide. At 0 (T0), 48 (T48) and 72 (T72) hours, the cells were incubated with ionomycin and PMA for 4 hours and with Brefeldin A for 2 hours to activate and induce protein production. After incubation, they were stained with antibodies to different cellular markers for FACS analysis to characterize the regulatory T-cells. The surface markers detected were CD4, CD8, CD25, DX5, and TGF-β. The intracellular markers detected were IL-4, IL-10, and IFN-γ.

In the FACS analysis, the lymphocytes were gated out from the forward/side scatter histograms; their double positive cell population percentages (i.e., CD4CD25, CD4DX5, CD8CD25, and CD8DX5) were read out from 2 channel fluorescence histograms. For calculating the triple positive cell population (i.e., CD4CD25IL-4, CD4CD25IL-10), the double positive cells were further gated, and their third channel reading in the histogram was used to multiply its original double positive ratio to generate the final triple positive population percentages.

Figure 6A:
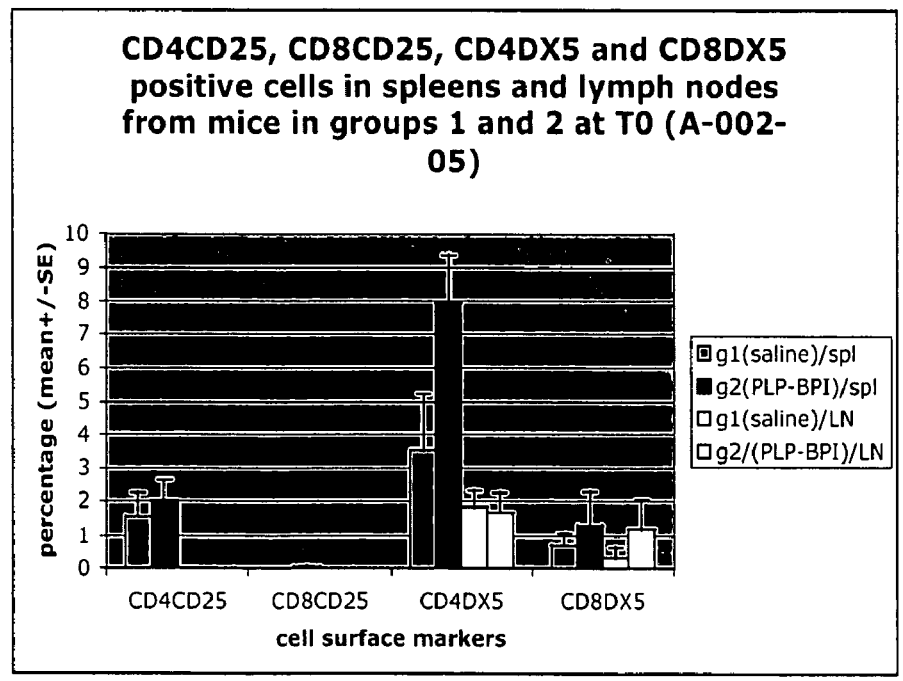
FIG. 6 shows CD4CD25, CD8CD25, CD4DX5, and CD8DX5 double-positive cells in spleens ("spl") and lymph nodes ("LN") of the mice in Group 1 (PBS-treated, g1) and Group 2 (PLP-BPI-treated, g2). The cells were harvested on day 15 when the treatment was completed; half of the mice in Group 1 developed EAE. Cells were analyzed at time points T0 (FIG. 6(A)), T48 (FIG. 6(B)), and T72 (FIG. 6(C)). n1=6, n2=6. p values are listed in the narrative.
Figure 6B:
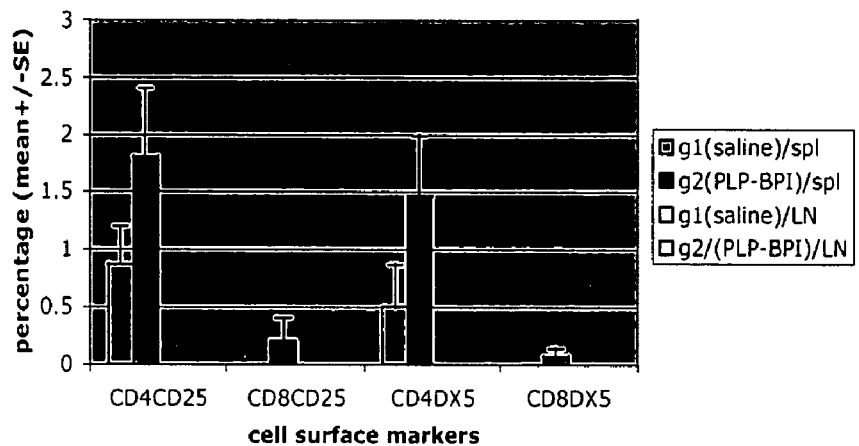
Figure 6C:
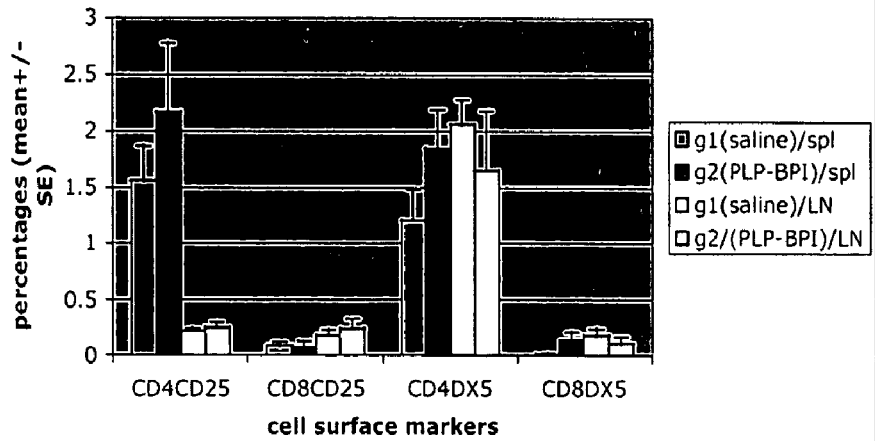

The results showed that CD8CD25 and CD8DX5 positive cells were hardly detectable in either spleen or lymph nodes after in vitro stimulation (T0, T48 and T72 time points, FIG. 6). There was no noticeable cell population difference in lymph nodes between Groups 1 and 2. The percentage of CD4CD25 T regulatory cells in the spleens of Group 2 seemed higher than that of Group 1 at T48 (Group 2=1.81±0.33% and Group 1=0.86±0.82%, p=0.2) and at T72 (Group 2=1.85±0.3% and Group 1=1.2±0.7%, p=0.4). However, there was no statistical significance between both groups at two time points. DX5 positive cells (CD4DX5, FIG. 6) also seemed higher in Group 2 than Group 1 spleens at time points of T48 (1.8±0.3% vs. 0.9±0.8%, p=0.19) and T72 (2.2±0.3% vs. 1.6±0.8%, p=0.17); however, there was no significant difference.

Figure 7A:
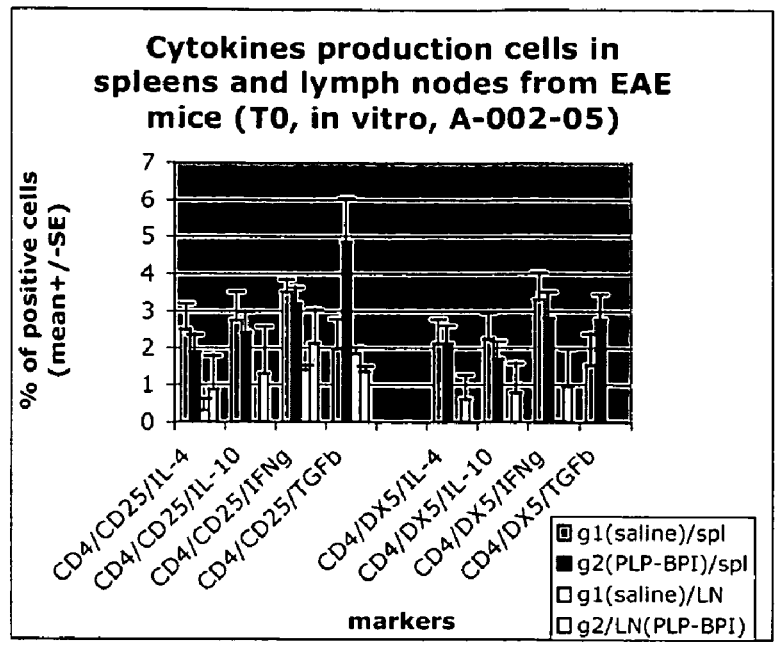
FIG. 7 shows cytokine-producing cells (CD4CD25IL-4, IL-10, IFN-γ or TGF-β; CD4DX5IL-4, IL-10, IFN-γ or TGF-β) in spleens ("spl") and lymph nodes ("LN"). PLP-BPI was given i.v. on days 4, 7, 10, and 14 at a dosage of 100 nmol/mouse to the mice in Group 2. PBS was administered to Group 1 as a control. The cells were harvested on day 15 when the treatment was completed; half of the mice in Group 1 developed EAE. These cells were stimulated in vitro with Mitomycin-treated syngeneic (SJL/J) splenocytes (1:10 ratio of the responders to stimulators) and PLP peptide. Cells were analyzed at T0 (FIG. 7(A)), T48 (FIG. 7(B)), and T72 (FIG. 7(C)) time points with n1=6 and n2=6 in Groups 1 and 2. p values are listed in Table 7.
Figure 7B:
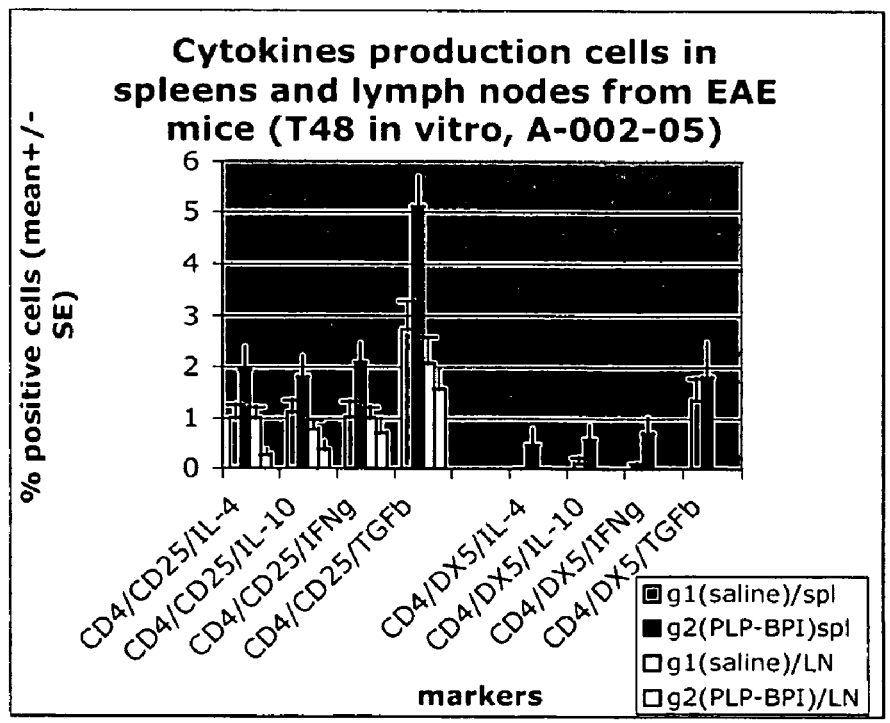
Figure 7C:
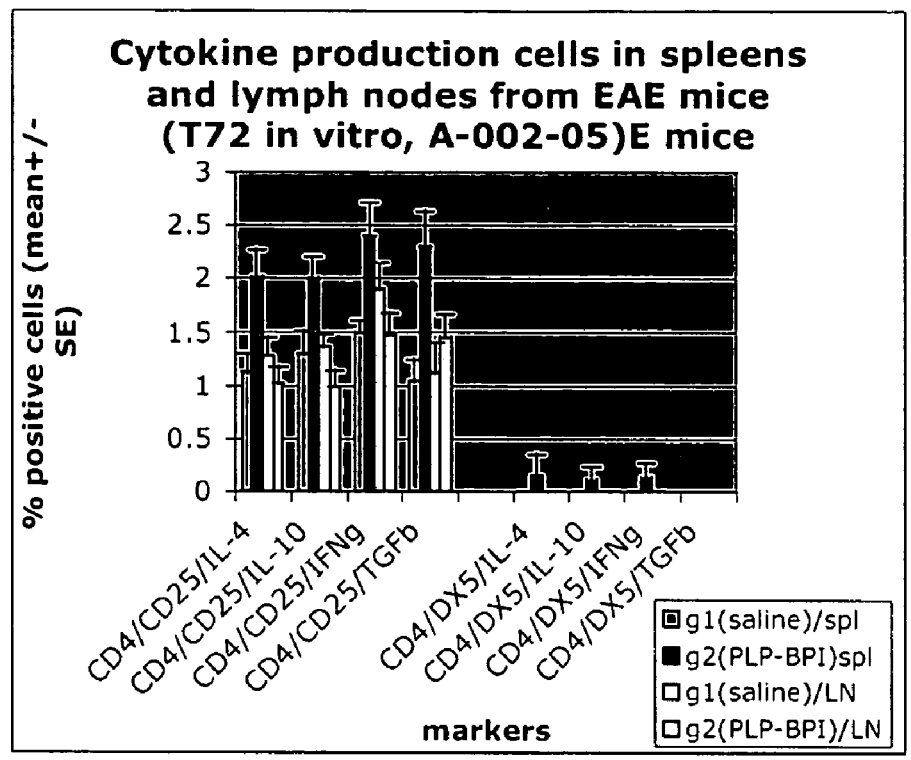

In contrast, there are prominent differences in lymphocyte populations in the spleens of Group 1 and Group 2 (FIG. 7, Table 7 for statistical analysis). It is interesting to note that PLP-BPI could significantly increase CD4CD25TGF-β, CD4CD25IL-4 and CD4CD25IL-10 populations in the mouse lymphocytes from spleens at the 72-hour time point (FIG. 7). These results indicate that PLP-BPI down-regulated autoimmune responses in EAE mice by stimulating the secretion of cytokines TGF-β, IL-4 and IL-10. CD4CD25TGF-β cells in the spleen were significantly higher in Group 2 than in Group 1 at all time points (T0, T48 and T72); Group 2 had significantly more CD4CD25IL-4, and CD4CD25IL-10 cells in spleens than did Group 1 at T72. It is well accepted that CD4CD25 lymphocytes are markers on T regulatory cells. TGF-β, IL-4 and IL-10 are considered Th2 regulatory cytokines, which play key roles in downregulation of autoimmune responses, especially to Th1-mediated autoimmune diseases such as EAE. These results suggest that PLP-BPI alters the cytokines profile that induces the suppressor phenotype of T-cells.

TABLE 7

Summary of statistical analysis (p values) of lymphocyte populations in the spleen using ANOVA analysis between Group 1 and Group 2.

| Time | CD4CD25 TGF-β | CD4CD25 IL-4 | CD4CD25 IL-10 | CD4CD25 IFN-γ | CD4CD25 | CD4 DX5 |
|---|---|---|---|---|---|---|
| T0  | 0.017* | 0.52   | 0.73   | 0.58  | 0.6 | 0.07 |
| T48 | 0.004* | 0.10   | 0.5    | 0.05  | 0.2 | 0.19 |
| T72 | 0.013* | 0.031* | 0.045* | 0.053 | 0.4 | 0.17 |

*p value < 0.05 is considered statistically significant

Example 4

PLP-BPI Efficacy Compared to VP2-PLP

To evaluate whether linking PLP and LABL peptides to give PLP-BPI has a significant role on its immunomodulatory activity, the activity of PLP-BPI was compared with that of a mixture of unlinked PLP and LABL peptides at the same concentration. To answer whether any antigenic peptide such as VP2 peptide that is linked to LABL peptide to give VP2-BPI will have immunomodulatory activity similar to that of PLP-BPI, we evaluated the activity of VP2-BPI in the same experiment. VP2$_{74-86}$ is an epitope peptide of Theiler's encephalomyelitis virus capsid protein VP2, and is known to bind to I-A$^s$. PBS-treated mice were used as the negative control. The experimental protocol was the same as in the previous study (see FIG. 1). Thus, VP2-BPI was used as a control to example to see if the PLP portion of the PLP-BPI is important to therapeutic activity.

Figure 8A:
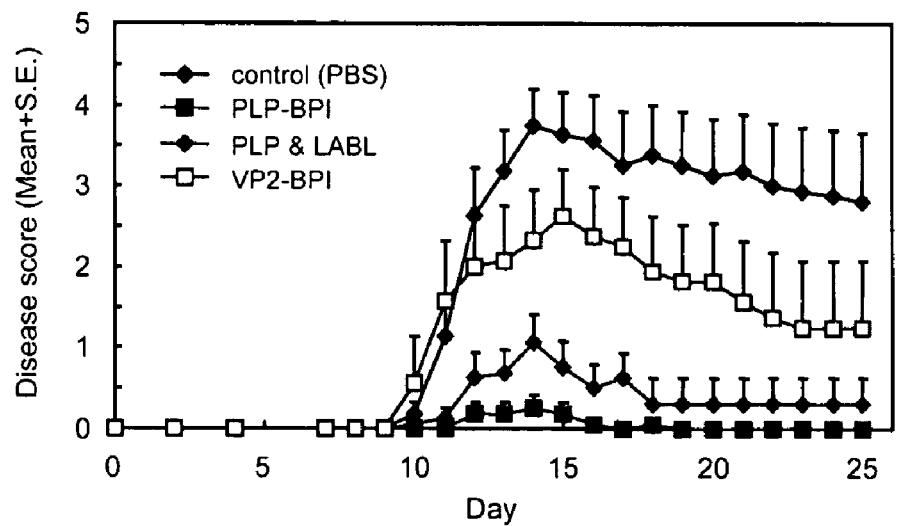
FIG. 8(A) shows the disease development.

The results show that PLP-BPI is a better molecule to suppress EAE than is a mixture of unlinked PLP and LABL peptides (FIG. 8(A)). There is a preliminary indication than a mixture of PLP and LABL peptides is better than treatment with PLP peptide alone (data not shown). On the other hand, VP2-BPI (SEQ. ID NO. 89) has lower modulatory activity than PLP-BPI, suggesting that linking any other antigenic peptide that binds to MHC-II will not provide activity similar to that of PLP-BPI. Compared to PBS-treated mice, VP2-BPI-treated mice have a better disease profile. One suggestion is that the LABL portion of VP2-BPI may block Signal-2 from LFA-1/ICAM-1 interaction on the T-cell:APC interface. Another suggestion is an inhibition of PLP-MHC (I-As) interaction by competitive binding of VP2-BPI to I-As.

Figure 8B:
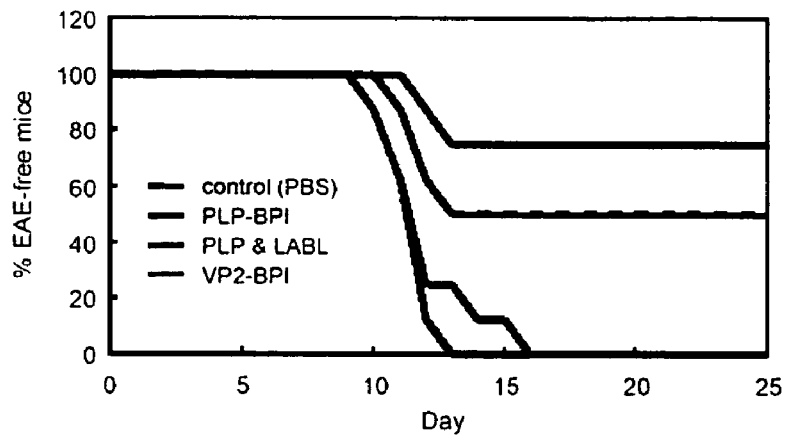
FIG. 8(B) shows the incidence of EAE.
Figure 8C:
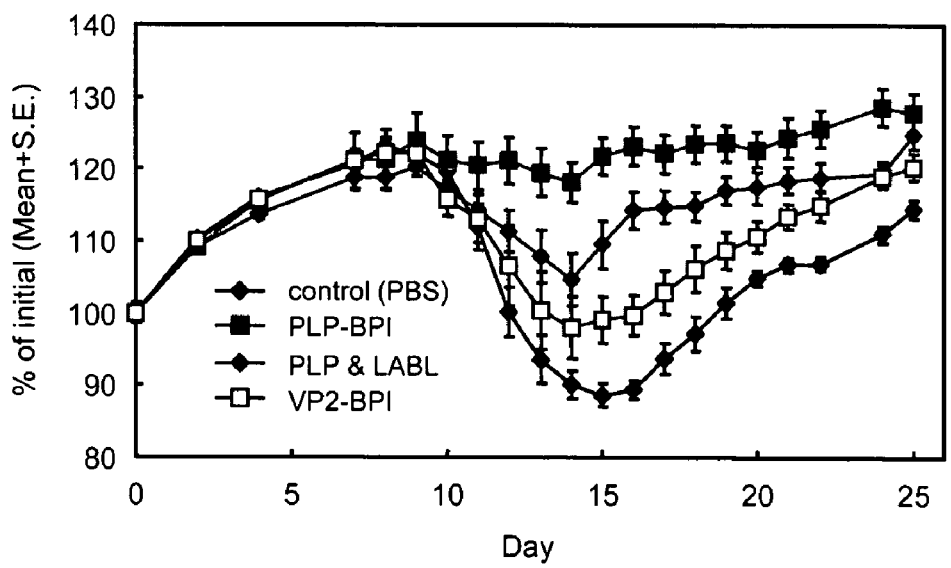
FIG. 8(C) shows changes in body weight of the animals.

PLP-BPI-treated mice had a lower disease incidence (~20%) than the mice treated with a mixture of PLP and LABL peptides (~55%) after day 17 (FIG. 8(B)). In contrast, both PBS-treated and VP2-BPI-treated mice had 100% disease incidence after day 17. In this particular experiment, there was very little loss of body weight in PLP-BPI-treated mice around day 14. A mixture of PLP and LABL peptides caused body weight loss around day 14. The severity of body weight loss was greatest in PBS-treated mice followed by VP2-BPI-treated mice (FIG. 8(C)). From these results, we can conclude that linking between PLP and LABL peptide is necessary for improved biological activity. In addition, the presence of the appropriate antigen such as PLP in BPI is necessary for PLP-BPI biological activity.

Example 5

Terminal Modifications to PLP-BPI

One way to improve the activity of a peptide is by improving its plasma stability. Because PLP-BPI has an uncapped N-terminus and C-terminus, it may have low plasma stability due to metabolism by amino-peptidases and carboxy-peptidases in the blood. This example investigated whether this problem can be overcome by capping the N-terminus and C-terminus by acetylation and amidation, respectively. Thus, Ac-PLP-BPI-NH$_2$, which is PLP-BPI molecule with acetylation and amidation at the N- and C-termini, respectively, was synthesized. However, this modification could influence the peptide's binding properties to its respective receptors. Hence, the activity of Ac-PLP-BPI-NH$_2$ was evaluated and compared with that of the uncapped parent PLP-BPI. At the same time, the effect of one vs. four injections of both molecules was compared.

Figure 9A:
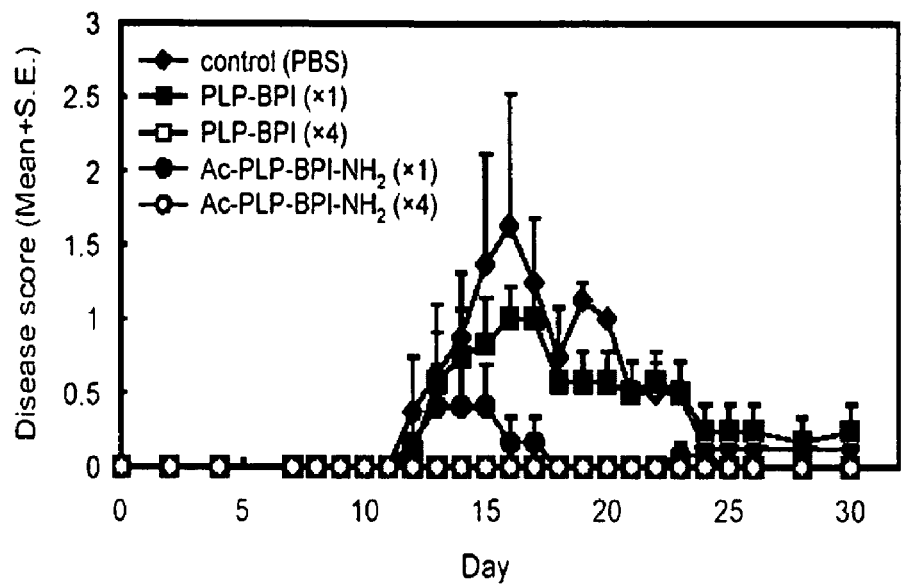
FIG. 9(A) shows the disease development.
Figure 9B:
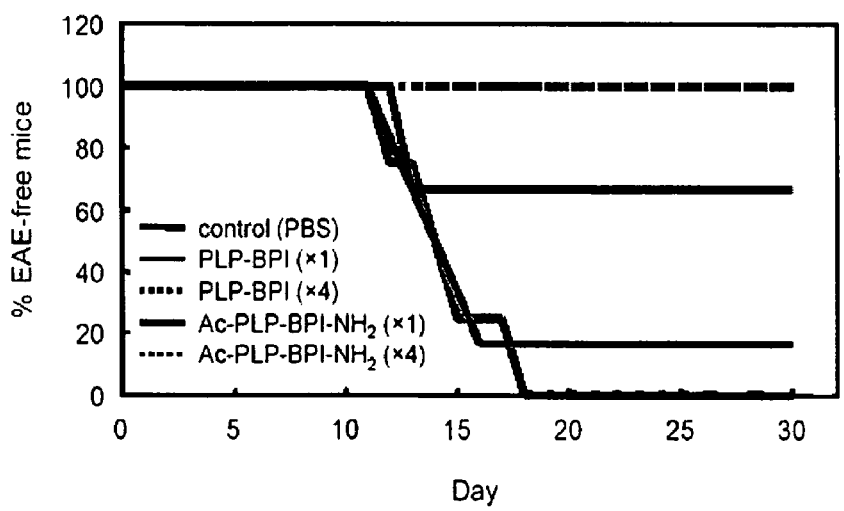
FIG. 9(B) shows the incidence of EAE.
Figure 9C:
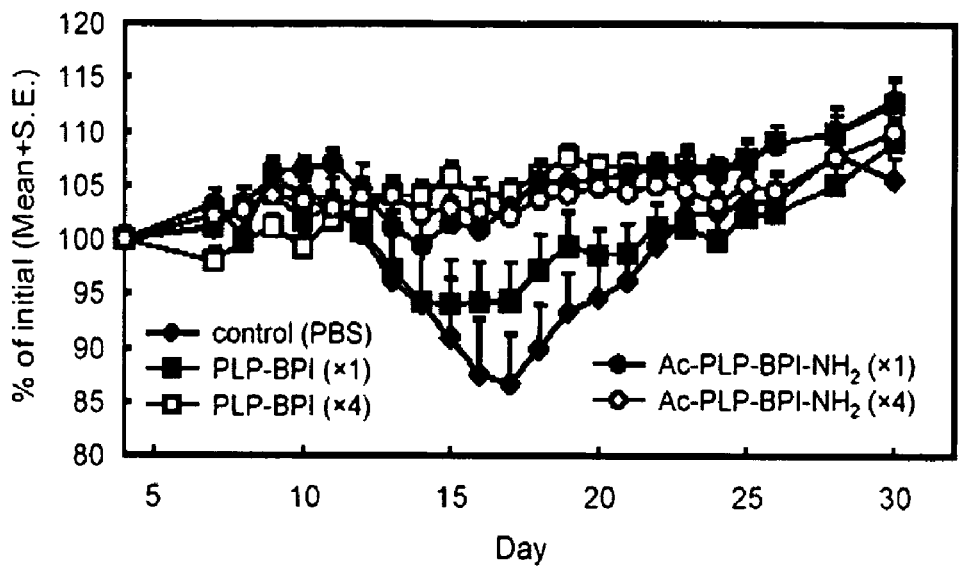
FIG. 9(C) shows changes in body weight of the animals.

Interestingly, Ac-PLP-BPI-NH$_2$ had better activity than the uncapped parent PLP-BPI. One injection of Ac-PLP-BPI-NH$_2$ can suppress the progression of EAE better than one injection of the parent PLP-BPI (FIG. 9(A)). Four injections of PLP-BPI are better than one injection. Using the disease score, it is difficult to differentiate the difference between four injections of Ac-PLP-BPI-NH$_2$ and PLP-BPI (FIG. 9(A)). However, they can be differentiated in the incidence of EAE (FIG. 9(B)). There was very limited fluctuation of body weight in animals treated with one or four injections of Ac-PLP-BPI-NH$_2$ (FIG. 9(C)). In conclusion, capping the N- and C-termini in Ac-PLP-BPI-NH$_2$ improved the immunomodulatory activity of the BPI molecule. This improvement may be used to lower the number of injections and dose of the BPI molecule to treat EAE. It can be theorized that the improvement in activity using Ac-PLP-BPI-NH$_2$ is due to the improvement of plasma stability and the improvement of binding properties to both I-A$^s$ and ICAM-1 on the surface of APC.

Example 6

Reduction of Anaphylactic Shock

In this example, the ability of BPI molecules to induce anaphylaxis after multiple injections was investigated. The procedures of Example 2 were followed with additional injection of PLP, PLP-BPI, or Ac-PLP-BPI-NH$_2$ peptide at day 30, and the mice were examined if they showed anaphylactic shock (Table 8). The PBS-treated mice had the highest incidence of anaphylaxis (75%) after being injected with PLP peptide at day 30. The animals treated with four injections of PLP-BPI or Ac-PLP-BPI-NH$_2$ prior to re-injection of the peptide at day 30 had the lowest incidence of anaphylaxis (16.7%). One treatment with Ac-PLP-BPI-NH$_2$ prior to re-injection of the peptide had 33.3% incidence of anaphylaxis while one treatment with PLP-BPI had a higher incidence of anaphylaxis (50%). Taken together, four treatments with Ac-PLP-BPI-NH$_2$ provided the best results with no EAE and low anaphylaxis. This suggests that future modifications of the Ac-PLP-BPI-NH$_2$ may improve the biological activity profile of this molecule for suppressing EAE.

TABLE 8

Anaphylaxis incidence after re-injection of the peptide at day 30

| Immunization | Peptide treatment | Peptide injection (day 30) | Moribund or death | Incidence of anaphylaxis |
|---|---|---|---|---|
| PLP/CFA | None (PBS) (day 4, 7, 10, 14) | PLP | 3/4 | 75.0% |
| PLP/CFA | PLP-BPI (day 4) | PLP-BPI | 3/6 | 50.0% |
| PLP/CFA | PLP-BPI (day 4, 7, 10, 14) | PLP-BPI | 1/6 | 16.7% |
| PLP/CFA | Ac-PLP-BPI-NH$_2$ (day 4) | Ac-PLP-BPI-NH$_2$ | 2/6 | 33.3% |
| PLP/CFA | Ac-PLP-BPI-NH$_2$ (day 4, 7, 10, 14) | Ac-PLP-BPI-NH$_2$ | 1/6 | 16.7% |

The less incidence of inducing anaphylactic shock by BPI molecules was further examined. Female SJL/J mice were immunized with PLP/CFA as above, and injected intravenously with PLP or BPI molecules (100 nmol/mouse) at later phase of the disease (i.e., between day 28 and day 35). Upon intravenous injection of PLP-BPI, the mice showed less incidence of anaphylaxis (35.7%) than PLP injection (75.0%) (Table 9, Experiment I). This was confirmed in another set of experiment, PLP-BPI induced anaphylaxis to 38.5% of treated mice while PLP caused anaphylaxis to more than 80% of treated mice (Table 9, Experiment II). In addition, 100% of mice that were injected with unlinked mixture of PLP and LABL (100 nmol each) died due to anaphylaxis. This suggests that the overall BPI structure is important for less incidence of anaphylaxis, not simply due to the presence of LABL peptide. Furthermore, it was confirmed in a separate set of experiment that Ac-PLP-BPI-NH$_2$ injection also showed less incidence of anaphylaxis to the mice than PLP injection (43.8% vs. 76.5%). Taken together, BPI molecules (including PLP-BPI and Ac-PLP-BPI-NH$_2$) could suppress EAE more efficiently with lower incidence of inducing anaphylaxis than PLP. This suggests that future modifications of the Ac-PLP-BPI-NH2 may improve the biological activity profile of this molecule for suppressing EAE.

TABLE 9

Anaphylaxis incidence after re-injection of the peptide at later phase of disease.

| Experiment | Immunization | Peptide | Incidence of anaphylaxis |
|---|---|---|---|
| I | PLP/CFA | PLP | 9/12 (75.0%) |
| | PLP/CFA | PLP-BPI | 5/14 (35.7%) |

TABLE 9-continued

Anaphylaxis incidence after re-injection of the peptide at later phase of disease.

| Experiment | Immunization | Peptide | Incidence of anaphylaxis |
|---|---|---|---|
| II | PLP/CFA | PLP | 11/13 (84.6%) |
| | PLP/CFA | PLP & LABL | 11/11 (100.0%) |
| | PLP/CFA | PLP-BPI | 5/13 (38.5%) |
| III | PLP/CFA | PLP | 13/17 (76.5%) |
| | PLP/CFA | Ac-PLP-BPI-NH$_2$ | 7/16 (43.8%) |

Example 7

Biotin-Labeled PLP-BPI

In this example, two examples of a PLP-BPI with a reporter molecule were prepared. In particular, two types of biotin-labeled PLP-BPI were synthesized:

EbHSLGKWLGHPDKF-AcGAcGAc-    (SEQ. ID No. 90)
ITDGEATDSG
and

HSLGKWLGHPDKF-AcEbAcGAc-    (SEQ. ID No. 91)
ITDGEATDSG, where Ac is aminocaproic acid and Eb is biotinyl-PEG-Glu (N-γ-(N-biotinyl-3-(2-(2-(3-aminopropyloxy)-ethoxy)-ethoxy)-propyl)-L-glutamine). The data shown here is for the N-terminal biotin-labeled PLP-BPI (EbHSLGKWLGHP-DKF-AcGAcGAc-ITDGEATDSG, SEQ. ID No. 90)), but similar binding property was observed with the other biotin-labeled PLP-BPI.

Figure 10:
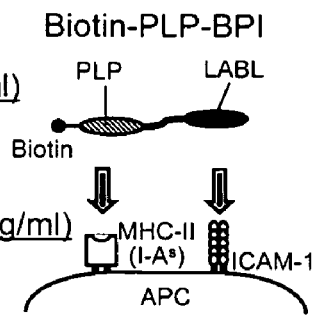
FIG. 10 shows the experimental sequence to detect binding of biotin-labeled PLP-BPI to B-cells.

An experimental protocol to study binding of biotin-labeled PLP-BPI to B-cells is shown in FIG. 10. Binding studies were done using mouse B-lymphocyte line LS102.9 (FIG. 11(A)) and the isolated B-cells from the spleen of female SJL/J mice after induction of EAE (FIG. 11(B)). For mouse B lymphocyte cell line LS102.9, these cells were cultured in modified Dulbecco's medium (ATCC 46-X) containing 0.05 mM 2-mercaptoethanol and 10% FBS. The surface expression of MHC-II (I-As) and ICAM-1 on LS102.9 cells was confirmed by using anti-I-As mAb (clone 10-3.6) and anti-CD54 mAb (clone 3E2), respectively. For the isolated spleen cells from EAE mice, the cells were isolated from female SJL/J mice on day 45 post immunization with PLP/CFA, when the clinical disease score for the mice was 0. Lymphocytes were obtained from the spleen cell suspension by centrifugation over Lymphocyte Separation Medium. T-cells were depleted by incubation with anti-CD90 mAb (clone G7) followed by Low-tox rabbit complement. Then, the cells were centrifuged over Lymphocyte Separation Medium to remove dead cells.

Figure 11:
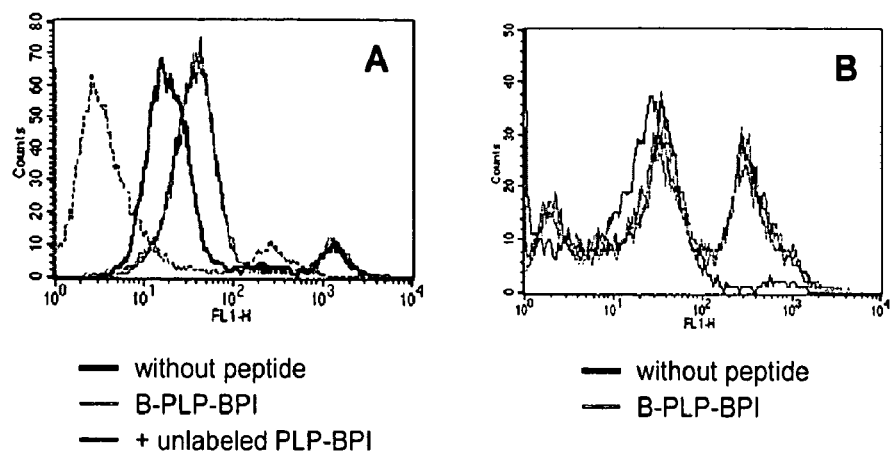
FIG. 11 shows the binding of B-PLP-BPI to (A) LS102.9 cells or (B) T-cell-depleted splenocytes. Biotin-labeled PLP-BPI (B-PLP-BPI; 50 μM) was incubated with LS102.9 mouse B-cells or T-cell-depleted splenocytes isolated from SJL/J female mice for 16 hours at 37° C. Then, the cells were incubated sequentially with fluorescein Avidin, biotinylated anti-Avidin, and fluorescein Avidin, and analyzed by flow cytometry. For competitive inhibition, B-PLP-BPI was incubated with the cells in the presence of unlabeled PLP-BPI (500 μM).

For the binding study, the biotin-labeled peptide (50 μM) was incubated with LS102.9 cells or T-cell-depleted splenocytes (2×106 cells) in 0.5% BSA-containing PBS for 16 hours at 37° C., 5% CO2. Following washing×3 with 5% FBS-containing PBS, the cells were incubated with fluorescein Avidin D (15 μg/ml) for 30 min at 4° C. The cells were further stained with biotinylated anti-Avidin D (1 μg/ml) for 60 min at 4° C., and then fluorescein Avidin D (15 μg/ml) for 30 min at 4° C. (each step was followed by washing×3). Finally, the fluorescein intensity of the individual cells was analyzed by flow cytometry. The results are illustrated in FIG. 11. The results show that biotinylated PLP-BPI (B-PLP-BPI, FIG.

11(A), green) binds to LS102.9 B-cell line. This binding can be inhibited by the parent PLP-BPI (un-labeled PLP-BPI, FIG. 11(A), pink line). Biotinylated PLP-BPI can also bind to the B-cells from the spleen of EAE-induced mice (FIG. 11(B), green). These results suggest that PLP-BPI can bind to B-cells from EAE mice and PLP-BPI can be used to diagnose the increase the amount of APC that recognizes the PLP-BPI.

PROPHETIC EXAMPLE

Use of PLP-BPI with Reporter Group as Diagnostic

Figure 12:
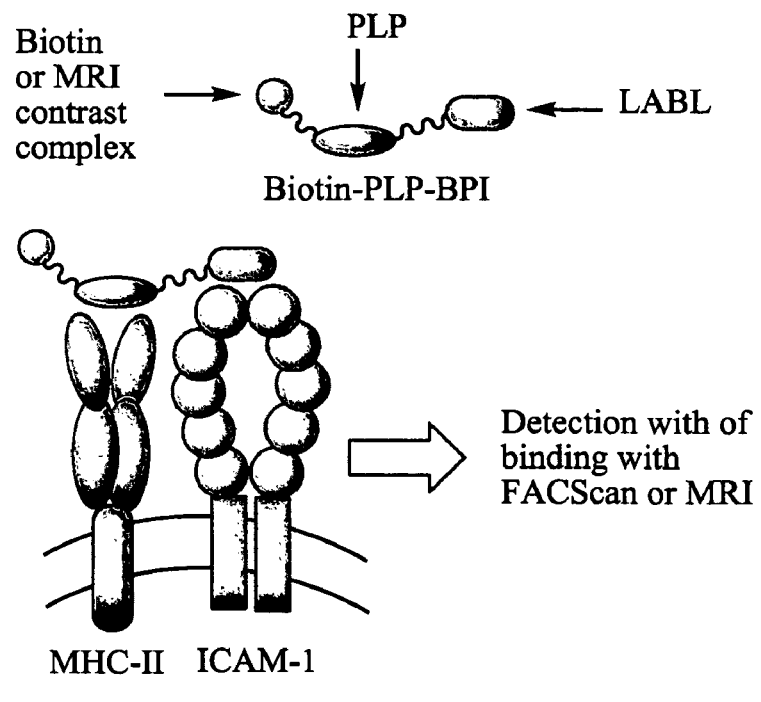
FIG. 12 is a schematic illustrating the biotin-tagged PLP-BPI binding (e.g. biotin-labeled PLP-BPI or Cplx-PLP-BPI) binding to an APC through the MHC-II and the ICAM-1 receptors on the APC.

The peptides of the present invention, such as the PLP-BPI, can be used to detect the increased in population APC populations that are related to the PLP antigen due to the activation by T-cells. In MS and EAE, a subpopulation of T-cells bind to APC that present PLP peptide(s) to form immunological synapse mentioned above. This subpopulation expands and produces cytokines for activation and proliferation of other T-cells (i.e., cytotoxic T-cells) and APCs (B cells, dendritic cells, and macrophages). For example, B-cells are activated to produce antibodies that recognize the antigen such as PLP. Thus, the number of APC, such as B-cells, that recognize PLP peptides is increased. Because PLP-BPI can bind simultaneously to MHC-II (e.g., I-A$^s$ in mice) and ICAM-1 on the surface of B-cells (FIG. 12), this PLP-BPI detects the increased number of APC such as B-cells in the white blood of MS patients compared to normal individual. It is expected that a higher population of APCs (i.e., B-cells) from white blood cells and spinal fluid of MS patients (greater than 30%) bind to PLP-BPI than that of APCs from normal individual. There are several ways to detect the binding of PLP-BPI to increase number of APC in the white blood cell of MS patient. For example, the biotinylated PLP-BPI will be incubated in the APC and detected with FACScan as shown above (FIG. 11).

PROPHETIC EXAMPLE

Use of PLP-BPI as Diagnostic Enhancing Agents in MRI

Figure 13:
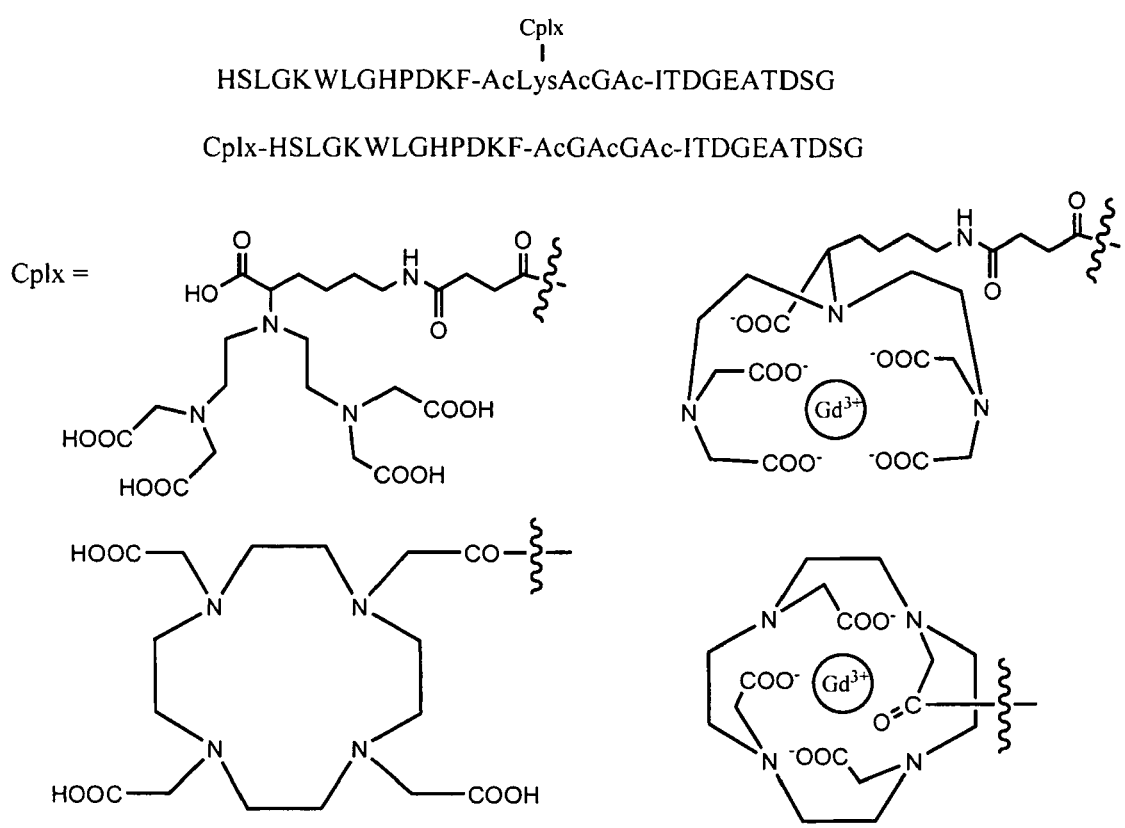
FIG. 13 is a schematic diagram of conjugates between PLP-BPI and MRI enhancing agents such as gadolinium complex (Cplx).

As mentioned previously, MRI has been used to diagnose MS by identifying the presence of myelin damage in the nerves in the brain and spinal cord in a form of lesions and plaques. These lesions are caused by the attack of the nerves by activated T-cells. Because these attacking T-cells are activated by APCs that present the myelin antigen(s), the lesion region is populated by activated T-cells and APCs. Because PLP-BPI binds to APCs, it can be used to localize and detect the high population of APCs surrounding the lesions. To accomplish this, PLP-BPI is conjugated with MRI enhancing (contrast) agents such as gadolinium complex to give Cplx-PLP-BPI as shown in FIG. 13 may be prepared. The complex may be directly linked to the BPI at the amino-terminus or at modified linker on the BPI itself, e.g. one in having a lysine residue, using techniques well known to those skilled in the art.

The Cplx-PLP-BPI can be injected to the spinal region of MS patients to localize activated APC around the lesions of the nervous systems. The advantage of this method is that Cplx-PLP-BPI can distinguish the lesions of MS from MRI unidentified bright spots (UBOs) from normal individual.

Figure 14:
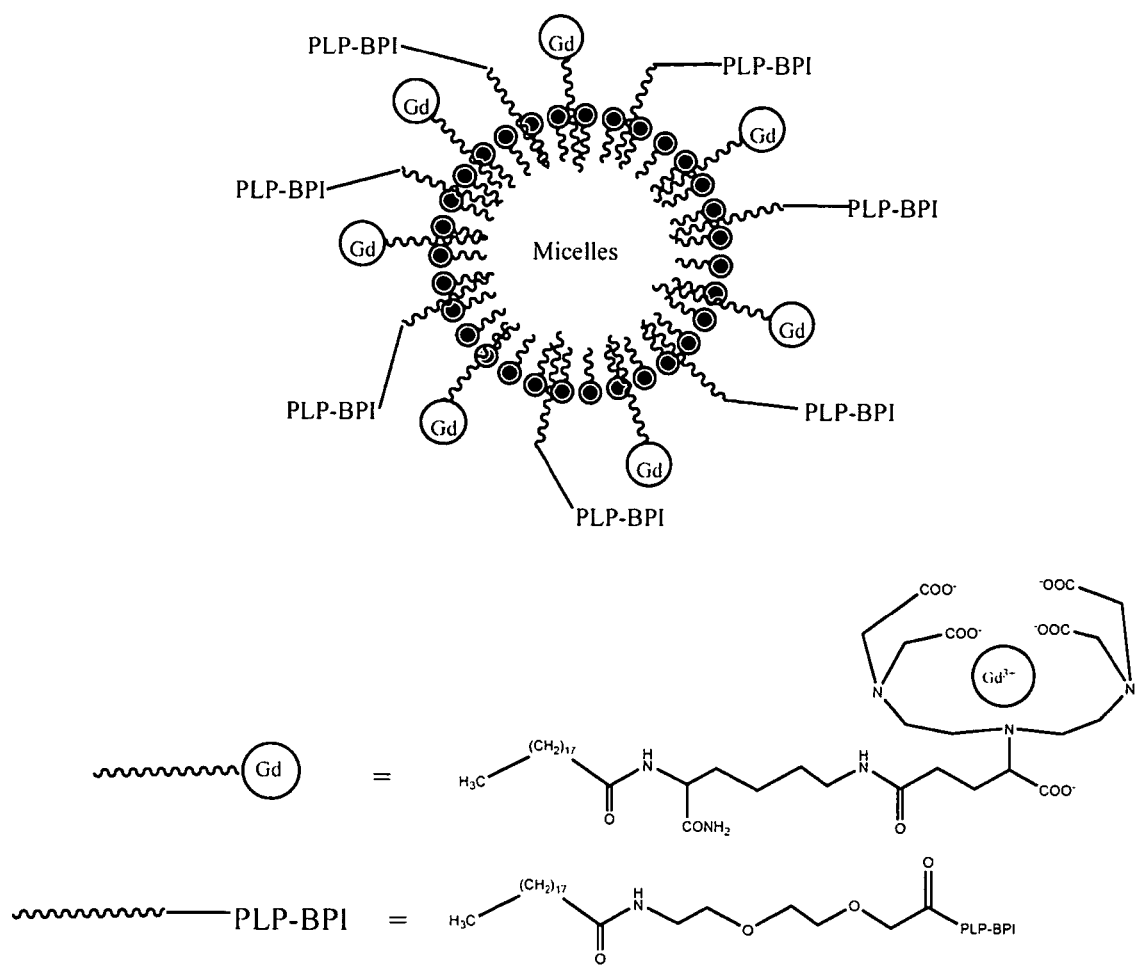
FIG. 14 is a schematic diagram of incorporation of PLP-BPI and gadolinium complex into micelles.

PLP-BPI can also be used to target gadolinium nanoparticles or micelles as shown in FIG. 14 to identify the population of APC around the plaques. In this example, the BPI is modified to have a long hydrophobic tail, for example:

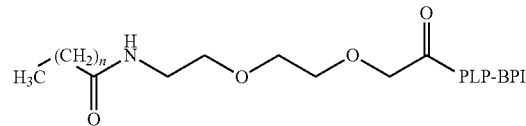

wherein n is an integer between 10 and 30. As before, the BPI may be covalently attached to the hydrophobic tail via the amino terminus or a lysine residue in the linker region of the BPI. Similarly, the contrast agent may be complexed with a molecule having a long hydrophobic tail. For example, in one aspect, the following modified gadolinium complex is provided:

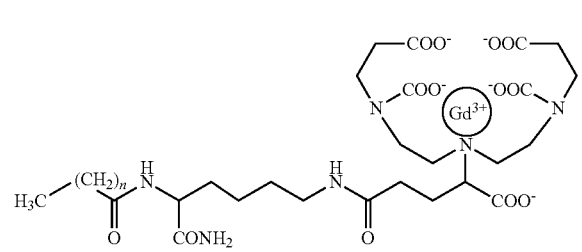

wherein n is an integer between 10 and 30. Such contrast agent complexes having a hydrophobic tail are set forth in Accoardo et al, *Physicochemical properties of mixed micellar aggregates containing CCK peptides and Gd complexes designed as tumor specific contrast agents in MRI*, J Am Chem Soc. Mar. 17, 2004; 126(10):3097-107, which are incorporated by reference. See also Lepinski et al., *MRI to detect atherosclerosis with gadolinium-containing immunomicelles targeting the macrophage scavenger receptor*, Magn Reson Med. September 2006; 56(3):601-10; Vaccaro et al., *Supramolecular aggregates of amphiphilic gadolinium complexes as blood pool MRI/MRA contrast agents*: physicochemical characterization, Langmuir. Jul. 18, 2006; 22(15):6635-43; Hovland et al., *Preparation and in vitro evaluation of a novel amphiphilic GdPCTA-[12] derivative; a micellar MRI contrast agent*, Org Biomol Chem. Feb. 21, 2003; 1(4):644-7; Tournier et al., *Gadolinium-containing mixed micelle formulations: a new class of blood pool MRI/MRA contrast agents*, Acad Radiol. May 2002; 9 Suppl 1:S20-8, which are incorporated by reference.

Figure 15:
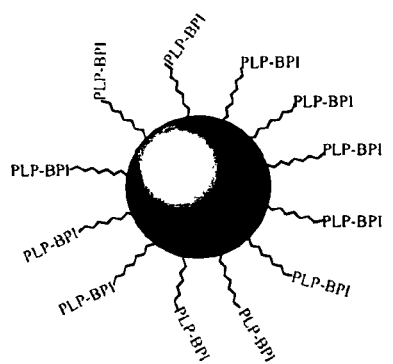
FIG. 15 is a schematic diagram of incorporation of PLP-BPI into PLGA nanoparticles via a covalent linker.
Figure 15:
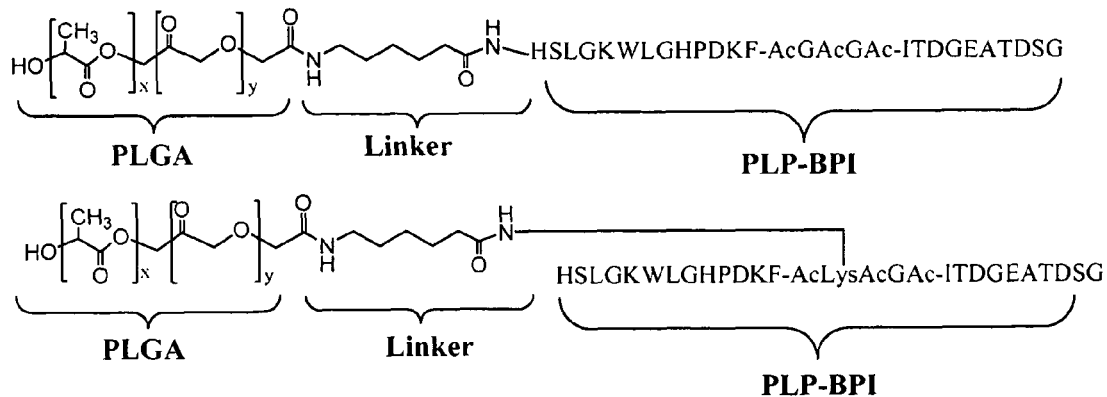

The BPIs may also be conjugated to the contrast agent via a polymeric particle as generally illustrated in FIG. 15. The particle is preferably a nanoparticle (i.e. a particle having an average particle size less than about 1000 nm), but larger particles may also be used. Suitable polymeric biomaterials include such as poly(DL-lactide-co-glycolide) (PLG), polylactic acid (PLA), or poly(lactic-co-glycolic acid) (PLGA). The contrast agent (Gd, iron oxide, and the like) is absorbed, doped or loaded onto the polymeric particle. See Faranesh et al., *In vitro release of vascular endothelial growth factor from gadolinium-doped biodegradable microspheres*, Magn Reson Med. June 2005; 51(6):1265-71. Berkland et al., *Fabrication of PLG microspheres with precisely controlled and monodisperse size distributions*, J Control Release May 18; 73(1):59-74 (2001); Zhu et al., *Biocompatible nanotemplate-engineered nanoparticles containing gadolinium: stability and relativity of a potential MRI contrast agent*, J Nanosci Nanotechnol. April 2006 6(4):996-1003; Anderson et al., *Magnetic resonance imaging of labeled T-cells in a mouse model of multiple sclerosis*, Ann. Neurol. May 2004 55(5): 654-9; which are incorporated by reference. The BPI may be covalently attached to the polymer forming the polymeric particle, e.g. PLGA, as set forth below:

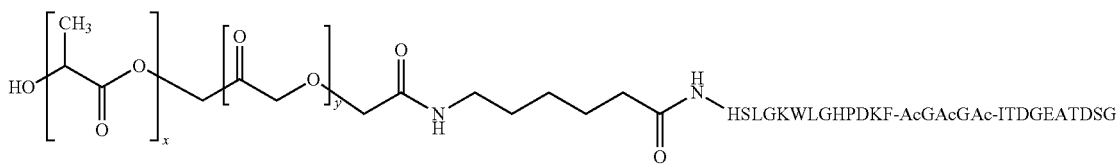

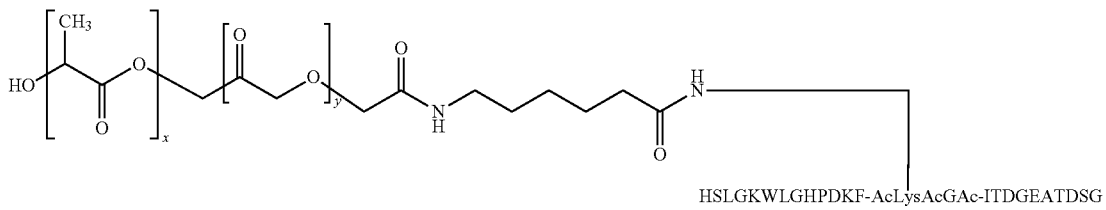

wherein X and Y are independently integers between 10 and 10,0000.

From the foregoing it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth or shown in the accompanying figures are to be interpreted as illustrative, and not in a limiting sense.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

The invention claimed is:

1. A bifunctional PLP-BPI peptide comprising a first peptide portion consisting of SEQ ID NO: 2 linked to a second peptide portion consisting of SEQ ID NO: 49.

2. The bifunctional peptide of claim 1, further comprising a linking portion.

3. The bifunctional peptide of claim 2, said linking portion having the general formula $(A,B)_x$, wherein A and B are amino acid residues, and said A amino acid residue of said linking portion is selected from the group consisting of aminocaproic acid, aminohexanoic acid, aminododecanoic acid, and β-alanine, and said B amino acid residue of said linking portion is glycine, and wherein X ranges from 1 to 100.

4. The bifunctional peptide of claim 2, said linking portion comprising at least one amino acid residue or polyethylene glycol.

5. The bifunctional peptide of claim 1 wherein a reporter group is covalently attached to said bifunctional peptide.

6. The bifunctional peptide of claim 5 wherein said reporter group is selected from the group consisting of enzymatic groups, photochemically reactive groups, chromophoric or fluorophoric groups, luminescent groups, radioactive groups, paramagnetic ions, thermochemically reactive groups, and one part of an affinity pair.

7. The bifunctional peptide of claim 5 wherein said reporter group is biotin or a gadolinium complex.

8. The bifunctional peptide of claim 7 wherein the peptide comprises
EbHSLGKWLGHPDKF-AcGAcGAc-ITDGEATDSG (SEQ ID NO: 90) or HSLGKWLGHPDKF-AcEbAcGAc-ITDGEATDSG, (SEQ ID NO: 91)
wherein Eb is N-γ-(N-biotinyl-3-(2-(2-(3-aminopropyloxy)-ethoxy)-ethoxy)-propyl)-L-glutamine.

9. The bifunctional peptide of claim 7 wherein said gadolinium complex is one of either:

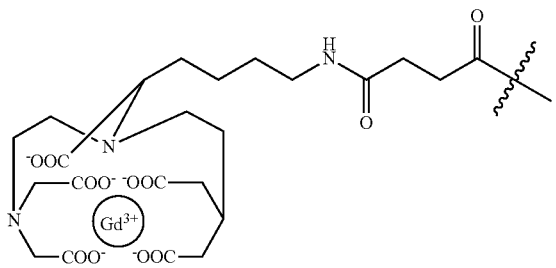

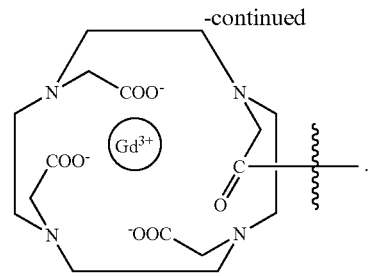

10. The bifunctional peptide of claim 1 wherein said bifunctional peptide is covalently attached to a $C_{10}$ to $C_{30}$ hydrophobic tail.

11. The bifunctional peptide of claim 10 which is

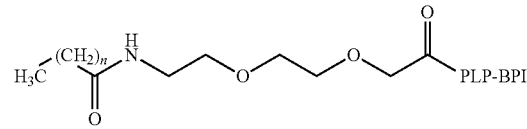

wherein n is an integer between 10 and 30, and PLP-BPI comprises a bifunctional peptide having a first peptide portion consisting of SEQ ID NO: 2 and second peptide portion consisting of SEQ ID NO: 49.

12. The bifunctional peptide of claim 10 wherein said bifunctional peptide has an amino terminus and a carboxy terminus, and wherein said $C_{10}$ to $C_{30}$ hydrophobic tail is covalently attached to the amino terminus of the PLP-BPI peptide.

13. The bifunctional peptide of claim 10 wherein said bifunctional peptide comprises a linking portion, and wherein said $C_{10}$ to $C_{30}$ hydrophobic tail is covalently attached to said linking portion.

14. The bifunctional peptide of claim 1 which is covalently linked to a polymeric particle loaded with a contrast agent.

15. The bifunctional peptide of claim 14 wherein said polymeric particle is poly(DL-lactide-co-glycolide) (PLG), polylactic acid, or poly(lactic-co-glycolic acid), and said contrast agent is gadolinium or iron oxide.

16. The bifunctional peptide of claim 1 which is SEQ ID NO: 86 (HSLGKWLGHPDKF-AcGAcGAc-ITDGEATDSG).

17. The bifunctional peptide of claim 1 having an amino terminus and a carboxy terminus, wherein said amino terminus is acetylated, and the carboxy terminus is amidated.

* * * * *